(12) United States Patent
Forbes

(10) Patent No.: US 8,865,688 B2
(45) Date of Patent: Oct. 21, 2014

(54) COMPOSITIONS AND METHODS FOR TREATMENT OF BOWEL DISEASES WITH GRANULATED MESALAMINE

(75) Inventor: William Forbes, Raleigh, NC (US)

(73) Assignee: Dr. Falk Pharma GmbH (DE)

( * ) Notice: Subject to any disclaimer, the term of this patent is extended or adjusted under 35 U.S.C. 154(b) by 211 days.

(21) Appl. No.: 12/573,081

(22) Filed: Oct. 2, 2009

(65) Prior Publication Data
US 2010/0086588 A1  Apr. 8, 2010

Related U.S. Application Data

(60) Provisional application No. 61/102,807, filed on Oct. 3, 2008, provisional application No. 61/109,708, filed on Oct. 30, 2008.

(51) Int. Cl.
*A61K 31/606* (2006.01)
*A61K 31/196* (2006.01)
*A61K 31/136* (2006.01)

(52) U.S. Cl.
CPC ............. *A61K 31/606* (2013.01); *A61K 31/196* (2013.01); *A61K 31/136* (2013.01)
USPC ........................................................ 514/166

(58) Field of Classification Search
None
See application file for complete search history.

(56) References Cited

U.S. PATENT DOCUMENTS

| | | | |
|---|---|---|---|
| 2,738,303 A | 3/1956 | Blythe | |
| 2,897,121 A | 7/1959 | Wagner | |
| 2,987,445 A | 6/1961 | Levesque | |
| 3,087,860 A | 4/1963 | Endicott | |
| 3,938,515 A | 2/1976 | Leeper et al. | |
| 4,138,475 A | 2/1979 | McAinsh et al. | |
| 4,432,966 A | 2/1984 | Zeitoun et al. | |
| 4,496,553 A | 1/1985 | Halskov | |
| 4,668,517 A | 5/1987 | Weber et al. | |
| 4,780,318 A | 10/1988 | Appelgren et al. | |
| 4,863,744 A | 9/1989 | Urquhart et al. | |
| 5,009,897 A | 4/1991 | Brinker et al. | |
| 5,171,580 A | 12/1992 | Iamartino et al. | |
| 5,178,866 A | 1/1993 | Wright et al. | |
| 5,472,710 A | 12/1995 | Klokkers-Bethke et al. | |
| 5,536,507 A | 7/1996 | Abramowitz et al. | |
| 5,541,170 A | 7/1996 | Rhodes et al. | |
| 5,643,602 A | 7/1997 | Ulmius | |
| 5,879,705 A | 3/1999 | Heafield et al. | |
| 5,945,124 A | 8/1999 | Sachs et al. | |
| 6,004,581 A | 12/1999 | Jepsen et al. | |
| 6,227,412 B1 | 5/2001 | Sweeton | |
| 6,277,412 B1 * | 8/2001 | Otterbeck | 424/490 |
| 6,423,340 B1 | 7/2002 | Ulmius | |
| 6,551,620 B2 | 4/2003 | Otterbeck | |
| 7,547,451 B2 | 6/2009 | Otterbeck | |
| 8,337,886 B2 | 12/2012 | Otterbeck | |
| 8,496,965 B2 | 7/2013 | Otterbeck | |
| 2006/0223787 A1 | 10/2006 | Devane et al. | |
| 2007/0043004 A1 | 2/2007 | Jepsen | |
| 2007/0167416 A1 * | 7/2007 | Johnson | 514/166 |
| 2007/0243184 A1 | 10/2007 | Fischkoff et al. | |
| 2008/0096849 A1 | 4/2008 | Johnson | |
| 2010/0035850 A1 * | 2/2010 | Karlstadt Meyeroff et al. | 514/166 |

FOREIGN PATENT DOCUMENTS

| | | |
|---|---|---|
| DE | 19732 903 A1 | 2/1999 |
| EP | 0040590 A2 | 11/1981 |
| EP | 0148811 A1 | 7/1985 |
| EP | 0278174 A2 | 8/1988 |
| EP | 0377477 A1 | 7/1990 |
| EP | 0453001 A1 | 10/1991 |
| EP | 0485840 A2 | 5/1992 |
| EP | 0629398 A1 | 12/1994 |
| EP | 0636370 A1 | 2/1995 |
| EP | 0671168 A1 | 9/1995 |
| FR | 2692484 A1 | 12/1993 |
| GB | 0 219 026 A | 6/1925 |
| WO | 87/01588 A1 | 3/1987 |
| WO | 91/07949 A1 | 6/1991 |
| WO | 92/16206 A1 | 10/1992 |
| WO | 93/07859 A1 | 4/1993 |
| WO | 96/29058 A1 | 9/1996 |
| WO | 97/23199 A1 | 7/1997 |
| WO | 2004093883 A2 | 11/2004 |

OTHER PUBLICATIONS

Kruis et al., "Once Daily Dosing of 3g mesalamine (Salofalk Granules) is Therapeutic Equivalent to a Three-Times Daily Dosing of 1g mesalamine for the Treatment of Active Ulcerative Colitis", Gastroenterology, vol. 127, Issue 4, pp. A-130-A-131, Abstract 898 (Apr. 2007).*

Salix Pharmaceuticals Announces Submisson of Granulated Mesalamine new Drug Application: Application Seeks Once-a-Day Dosing for Maintenance of Remission of Ulcerative Colitis. New Release [online]. Salix Pharmaceuticals, Apr. 20, 2008 [retrieved on Nov. 18, 2009]. Retrieved from the Internet: <URL: http://web.archive.org/web/20080420074304/http://salix.com/news/stories/20071231.aspx> p. 1, para. [0002]; ti.

Xifaxan Trials Initiated in C. difficile—Associated Diarrhea, Irritable Bowel Syndrome and Hepatic Encelophalopathy. New Article [online]. EndoNurse, Jan. 12, 2006 [retrieved on Nov. 18, 2009]. Retrieved from the Internet: <URL: http://www.endonurse.com/hotnews/61h1216383748345.html> p. 2, para [0001].

(Continued)

Primary Examiner — David J Blanchard
Assistant Examiner — Barbara Frazier
(74) Attorney, Agent, or Firm — McCarter & English LLP; Jonathan M. Sparks; Michael J. DeGrazia

(57) ABSTRACT

Disclosed are methods for treating gastrointestinal disorders, e.g., Crohn's disease, ulcerative colitis, and diverticular disease, with a granulated mesalamine formulation. Some formulations use granulated mesalamine in capsule form. Also included are methods to extend remission of ulcerative colitis by administration of a once-daily dosage of granulated mesalamine.

16 Claims, 3 Drawing Sheets

(56) References Cited

OTHER PUBLICATIONS

New Once Daily Salofalk Granules Launced for Ulcerative Colitis. News Article [online]. Medical News Today, Feb. 17, 2008 [retrieved on Nov. 18, 2009]. Retrieved from the internet: <URL: http://web.archive.org/web/20080217225137/jhht://www.medicalnewstoday.com/articles/96533.php. p. 1, para [0001]-[0003]; p. 2, para. [0001], [0004]-[0005].

Asacol (Mesalazine). NetDoctor, Aug. 4, 2008 [online] [retrieved on Nov. 21, 2009]. Retrieved from the Internet <URL: http://web.archive.org/web/20080804202621/http://www.netdoctorco.uk/medicines/100002331.html> p. 1-2.

Mesalamine (Oral). Consumer Information [online]. Drugs.com, Jun. 25, 2008, [retrieved on Nov. 21, 2009]. Retrieved from the Internet: <URL: http://web.archive.org/web/20080625022554/http://www.drugs.com/cons/mesalamine.html> p. 1-3.

Kotanagi et al. Pancytopenia Associated with 5-aminosalicylic Acid use in a Patient with Chrone's Disease. Jouranl of Gastroenterology. Jul. 1998, vol. 33, No. 4, (abstract) [online] [retrieved on Nov. 21, 2009]. Retrieved from the Internet: <URL: http://www.spingerlink.com/content/rvyy97eylgwfpt2r/> ab.

Pica et al. Oral Mesalazine (5-ASA) Treatment May Protect Against Proximal Extension of Mucosal Inflammation in Ulcerative Proctitis. Inflammatory Bowel Diseases, Nov. 2004, vol. 10, No. 6, pp. 731-736, [online] [retrieved on Nov. 22, 2009]. Retrieved from the Internet: <URL: http://www3.interscience.wiley.com/cgi-gin/fulltext/113521900/PDFSTAT> p. 731, col 1, para {0002], [0004]; p. 732, col. 1, para. [000]-[0002]; p. 733, col. 1, para. [0003]; p. 733, col. 2, para [0002]-[0003]; p. 735, col. 1, para [0002]; p. 735, col. 2, para [0002].

Analysis Shows Treatment Response to Mesalamine Associated with Rapid Mucosal Healing in Patients with Moderately Active Ulcerative Colitis. Medical News Today, Oct. 25, 2006, [online] [retrieved on Nov. 22, 2009]. Retrieved from the Internet: <URL: http://www.medicalnewstoday.com/articles/54958.php> p. 1, para {0001], [0003]-[0004]; p. 2; para [0001], [0007]-[0008].

Lichtenstein, Gary et. al., "Once-Daily 1.5-G Granulated mesalamine Effectively Maintains Remission in Patients with Ulcerative Colitis Who Switch from Different 5-ASA Formulations" American Journal of Gastroenterology, vol. 103, No. Suppl. S, 1100 Sep. 2008, pp. S429-S430, XP009156858, & 73rd Annual Meeting of the American-College-of-Gastroenterology; Orlando, FL, USA; Oct. 3-8, 2008.

"Salix Announces Statistically Significant Top-Line Results of a Unique Granulated Mesalamine Product Registration Study in Ulcerative Colitis" Drugs.com [Online] Sep. 5, 2007, pp. 1-2, Retrieved from the Internet: [retrieved on Aug. 17, 2012].

Raedler, A., et al., "Mesalazine (5-aminosalicylic acid) micropellets show similar efficacy and tolerability to mesalazine tablets in patients with ulcerative colitis—results from a randomized-controlled trial," Alimentary Pharmacology & Therapeutics, vol. 20, No. 11-12, Dec. 2004, pp. 1353-1363 (XP002670377).

Hogan, J.E., "Hydroxypropylmethylcellulose sustained release technology," Drug Dev. Ind. Pharm. 15:975-99 (1989).

http://eudragit.evonik.com/product/eudragit/en/products-services/eudragit-products/sustained-release-formulations/Pages/default.aspx [downloaded Apr. 2, 2014].

http://www.ibdcare.co.uk/controversy/in-ulcerative-colitis.htm [downloaded Mar. 16, 2014].

Hypromellose. (2009). In Handbook of Pharmaceutical Excipients (Rowe et al. eds., 6th ed. pp. 326-329).

Jantzen, G. & Robinson, J., "Sustained and controlled-release drug delivery systems." Modern Pharmaceutics, 3rd Ed. 1995.

John, V., et al., "Gastrointestinal Transit of Oros Drug Delivery Systems in Healthy Volunteers: A Short Report," Brit. J. Clinical Pharmacology 19:203S-206S (1985).

Joshi, S., "Sol-Gel Behavior of Hydroxypropyl Methylcellulose (HPMC) in Ionic Media Including Drug Release," Materials 4:1861-1905 (2011).

Kabir, M.A. & J.P. Reo, "Hydroxypropyl Cellulose," in Handbook 6th Ed. 317-322, (Revised Feb. 2009).

Kadiyala, I. et al., "The study of marketed and experimental formulation approaches enabling site-specific delivery of mesalamine in patients with inflammatory bowel disease," Recent patents on drug delivery & Formulation 7:1-9 (2013).

Kakoulides, E., et al., "Azocrosslinked poly(acrylic acid) for colonic delivery and adhesion specificity: in vitro degradation and preliminary ex vivo bioadhesion studies," J. Controlled Release 54:95-109 (1998).

Kane, S., et al., "Medication Nonadherance and the Outcomes of Patients with Quiescent Ulcerative Colitis," The American Journal of Medicine 114:39-43 (2003).

Karbach, V., et al., "Extent of Drug Compliance in Crohn Disease Patients—Study of a Special Ambulatory Care Unit of a University Clinic" Gastroenterol 22:573-579 (1984).

Kiefer, E., "Medical management of chronic ulcerative colitis," Lahey Clinic Bulletin 12:236-241 (1962).

Zainal, N., et al., "Oral Disopyramide for the Prevention of Arrhythmias in Patients with Acute Myocardial Infarction with Admitted to Open Wards," Lancet 2:892-895 (1977).

Kinget, R., et al., "Review Article: Colonic Drug Targeting," J. of Drug Targeting 6:129-149 (1998).

Klotz, U et al., "A new slow-release form of 5-aminosalicylic acid for the oral treatment of inflammatory bowel disease," Drug Res. 35:636-639 (1985).

Kocherbitov, V., et al, "Hydration of microcrystalline cellulose and milled cellulose studied by sorption calorimetry," J. Phys Chem B. 112(12):3728-3734 (2008).

Korsmeyer, R., et al., "Mechanisms of Potassium Chloride Release from Compressed, Hydrophilic, Polymeric Matrices: Effect of Entrapped Air," Journal of Pharmaceutical Sciences 72(10):1189-1191 (1983).

Krowczynski, L., "Oral extended-release dosage forms: Principles of technology," Extended-Release Dosage Forms pp. 97-158 (1987).

Lachman, L., et al., "Sustained Release Dosage Forms," The theory and practice of industrial pharmacy pp. 430-456 (1986).

Lansoprazole Delayed-Release Capsules. (2010). In the United States Pharmacopeia (34th ed., pp. 3270-3271).

Layer, P., et al., "Delivery and fate of oral mesalamine microgranules within the human small intestine," Gastroenterology 108(5):1427-1433 (1995).

Lehmann K. & D. Dreher, D., "Coating of Tablets and Small Particles with Acrylic Resins by Fluid Bed Technology," Int'l J. Pharmaceutical Technology & Product Manufacture 2(4):31-43 (1981).

Leopold, C., "Coated dosage forms for colon-specific drug delivery," Pharm. Sci. & Tech. Today 2(5):197-204 (1999).

Leopold, C., "Eudragit® E as coating material for the pH-controlled drug release in the topical treatment of inflammatory bowel disease (IDB)," Journal of Drug Targeting 6(2):85-94 (1998).

Li, C., et al, "The use of hypromellose in oral drug delivery," J Pharm Pharmacol 57(5): 533 (2005).

Lichtenstein, G., "Mesalamine in the Treatment of Ulcerative Colitis: Novel Therapeutics Options," 5 Gastroenterology & Hepatology 5(1):65-73 (2009).

Lichtenstein, G., et al., "Review article: 5-aminosalicylate formulations for the treatment of ulcerative colitis—methods of comparing release rates and delivery of 5-aminosalicylate to the colonic mucosa," Alimentary Pharmacology & Therapeutics 28:663-673 (2008).

Lin, C., et al, "Hydrogels in controlled release formulations: Network design and mathematical modeling," Adv Drug Deily Rev 58:1379-1408 (2006).

Meglumine. (2009). In Handbook of Pharmaceutical Excipients (6th ed., pp. 431-432).

Melia, C., et al., "Structure and behaviour of hydrophilic matrix sustained release dosage forms: 1. The origin and mechanism of formation of gas bubbles in the hydrated surface layer," Int'l J. of Pharmaceutics 100(1-3):263-269 (1993).

Melia, C., "Hydrophilic Matrix Sustained Release Systems Based on Polyscaccharide Carriers," Critical Reviews in Therapeutic Drug Carrier Systems 8(4):395-421 (1991).

(56) References Cited

OTHER PUBLICATIONS

Melia, C., et al., "Advantages and Disadvantages of Multiparticulate Dosage Systems," Multiparticulate oral dosage forms: technology and biopharmaceutics Melia, Washington & Wilson eds., pp. 136-142 (1994).
Mesalamine Extended Release Capsules. (1997). In The United States Pharmacopeia (23rd ed., pp. 3905-3906).
Mesalamine Extended-Release Capsules. (1994). In Pharmacopeial Forum 20(1):6757-6846.
Mesalamine Extended-Release Capsules. (2010). In the United States Pharmacopeia (34th Revision, pp. 3430).
Mesalamine Extended-Release Capsules. (2013). In US Pharmacopeia (36th Revision, pp. 4255-4256).
Mesalazine. (1991). In Therapeutic Drugs 2:M70-M73 (Dollery ed.).
Miller, S. et al., "Effect of poloxamer 407 gel on the miotic activity of pilocarpine nitrate in rabbits" Int. J. Pharmaceutics 12:147-152 (1982).
Milojevic, Snezana et al., "Amylose as a coating for drug delivery to the colon: Preparation and in vitro evaluation using 5-aminosalicylic acid pellets," J. Controlled Release 38:75-84 (1996).
Morphine Sulfate (1996). In The Merck Index (12 ed. p. 6359).
Morphine. (1999). In Therapeutic Drugs 1:M225-232 (Dollery ed.).
Moustafine, R., et al., "Physicochemical characterization and drug release properties of Eudragit E PO/Eudragit® L 100-55 interpolyelectrolyte complexes," European Journal of Pharmaceutics and Biopharmaceutics 63:26-36 (2006).
Muller, A., et al., "Experience of 5-aminosalicylate nephrotoxicity in the United Kingdom" Alimentary Pharmacology and Therapeutics 21:1217-1224 (2005).
Müllers, I., et al., "Production of dosage forms for oral drug delivery by laminar extrusion of wet masses," Eur. J. Pharmaceutics Biopharmaceutics 84:626-632 (2013).
Muraoka, M., et al., "Evaluation of intestinal pressure-controlled colon delivery capsule containing caffeine as a model drug in human volunteers," J. of controlled Release 52:119-129 (1998).
Narasimhan, B. & Peppas, N. "Disentanglement and Reptation During Dissolution of Rubbery Polymers," J. Polym. Sci., Polym. Phys. 34:947-961 (1996).
Adkin, D., et al., "Colonic transit of different sized tablets in healthy subjects." J. Cont. Release 23:147-156 (1993).
Alderman D., "A review of cellulose ethers in hydrophilic matrices for oral controlled-release dosage form." Int J Pharm Tech Prod Manuf 5:1-9 (1984).
Alvarez, L. et al, "Effect of Microcrystalline Cellulose Grade and Process Variables on Pellets Prepared by Extrusion-Spheronization." Drug Develop Ind Pharm 28:451-456 (2002).
Asacol. (1996). In Physician's Desk Reference (50th ed., pp. 1979-1981).
Asacol. (1998). In Physician's Desk Reference (52d ed., pp. 2312-2313).
Asacol. (1999). In Physician's Desk Reference (53d ed., pp. 2538-2539).
Ashford, M., et al., "Targeting Drugs to the Colon: Delivery Systems for Oral Administration." J. Drug Targeting 2:241-258 (1994).
Ashford, M., et al., "An In Vivo Investigation into the Suitability of pH Dependent Polymers for Colonic Targeting." Int'l J. Pharm. 95:193-199 (1993).
Azulfidine. (1997). In Physician's Desk Reference (51st ed., pp. 2059-2060).
Azulfidine. (1998). In Physician's Desk Reference (52d ed., pp. 2239-2241).
Azulfidine. (1999). In Physician's Desk Reference (53d ed., p. 2454).
Badawi, A., et al., "Drug Release from matrices made of polymers with reacting sites." International Journal of Pharmaceutics 5: 55-62 (1980).
Banerjee, S., et al., "Compressive textural attributes, opacity and syneresis of gels prepared from gellan, agar and their mixtures." Journal of Food Engineering 102:287-292 (2011).

Barrow, L. et al., "Pathological influences on colonic motility: implications for drug delivery." Adv. Drug Delivery Reviews 7:201-218 (1991).
Barry, M., "Selected side-effects: 9. Mesalazine and renal impairment." Prescriber's Journal 32:205-209 (1992).
Bettini, R. et al, "Polymer relaxation in swellable matrices contributes to drug release." Proceed Int Symp Control Rel Bioact Mater 25:36-37 (1998).
Bettini, R., et al, "Swelling and drug-release in hydrogel matrices—polymer viscosity and matrix porosity effects." Eur J Pharm Sci 2: 213-219 (1994).
Brzezinski, A., et al., "Use of old and new oral 5-aminosalicylic acid formulations in inflammatory bowel disease." Cleveland Clinical Journal of Medicine 62:317-323 (1995).
Budesonide. (1999). In Therapeutic Drugs 1: B88-92 (Dollery ed.).
Campregher, C., "Aminosalicylates. Best Practice & Research Clinical Gastroenterology." 25: 535-546 (2011).
Carothers, W., "Polymers and polyfunctionality" Trans Faraday Soc 32: 39-49 (1936).
Chambliss, W., "Enteric Coatings" In Encyclopedia of Pharmaceutical Technology 5 (1992).
Chang, R., et al., "Sustained Drug Release in Tablets and Particles Through Coating." In Pharmaceutical Dosage Forms: Tablets 199-302 (Lieberman et al., eds. 2nd Ed. 1990).
Chatlapalli R., et al, "Physical characterization of HPMC and HEC and investigation of their use as pelletization aids." Intl Journal of Pharmaceutics 161: 179-93 (1998).
Christensen, L., et al., "Topical and systemic availability of 5-aminosalicylate: comparisons of three controlled release preparations in man." Aliment. Pharmacol. Therap. 4: 523-533 (1990).
Coffey, D., et al, "Cellulose and cellulose derivatives." In Food polysaccharides and their applications (Marcel Dekker, NY, pp. 125-153) (1995).
Cohen, R., "Review article: evolutionary advances in the delivery of aminosalicylates for the treatment of ulcerative colitis." Alimentary Pharmacology & Therapeutics 24:465-474 (2006).
Cohen, R., "Is There a Role for Rectal Therapy in the Treatment of Inflammatory Bowel Disease?" Gastroenterology & Hepatology 6:309-316 (2010).
Colombo, P., et al., "Drug release modulation by physical restrictions of matrix swelling." Int J Pharm 63:43-48 (1990).
Colombo, P., et al., "Swelling-controlled release in hydrogel matrices for oral route." Adv Drug Deliv Rev 11: 37-57 (1993).
Colombo, P., et al., "Sweallable matrices for controlled drug delivery: gel-layer behavior, mechanisms and optimal performance." PSTT 3:198-204 (2000).
Columbo, P., et al., Chapter 9 in Handbook of Pharmaceutical Controlled Release Technology. (D. Wise ed., p. 183-209) (2000).
Corrigan, G., et al., "Review article: interstitial nephritis associated with the use of mesalazine in inflammatory bowel disease." Alimentary Pharmacology & Therapeutics 14:1-6 (2000).
Costa, R, et al., "Modeling and Comparison of Dissolution Profiles." Eur J Pharm Sci 13:123-133 (2001).
Coupe, A., et al., "Variation in Gastrointestinal Transit of Pharmaceutical Dosage Forms in Healthy Subjects," Pharmaceutical Research 8:360-364 (1991).
D.I. No. 118—Order Construing the Terms of U.S. Patent Nos. 6,551,620; 7,547,451; 8,337,886; and 8,496,965 (Dec. 17, 2013).
Daniel-da-Silva, A., et al, "Impact of Magnetic Nanofillers in the Swelling and Release Properties of K-Carrageenan Hydrogel Nanocomposites," Carbohyd Polym 87: 328-335 (2012).
Daumesnil, R., "Marketing Considerations for Multiparticulate Drug Delivery Systems." in Multiparticlate Oral Drug Delivery 457-475 (Ghebre-Sellassie ed., 1994).
Davis, S., et al., "Gastrointestinal Transit of a Multiparticulate Tablet Formulation in Patients with Active Ulcerative Colitis." Int'l J. Pharmaceutics 68:199-204 (1991).
Davis, S. et al. "Transit of pharmaceutical dosage forms through the small intestine." Gut 27:886-892 (1986).
Davis, S., "The Design and Evaluation of Controlled Release Systems for the Gastrointestinal Tract." J. Cont. Release 2:27-38 (1985).

(56) References Cited

OTHER PUBLICATIONS

De Souza, Dayse Fernanda, et al., "Development of enteric coated sustained release minitablets containing mesalamine." Brazilian J. of Pharmaceutical Sciences 529-536 (2013).
Deasy, Patrick B., Chapter 2: Core and Coating Properties 21-60 & Chapter 7: Air Suspension Coating 161-179 in Microencapsulation and Related Drug Processes. (1984).
Deo, S.C., et al., "Development of mesalazine pellets coated with methacrylic-derived polymer." Brazilian Journal of Pharmaceutical Sciences 47:103-109 (2011).
Dew, M.J., et al. "5-aminosalicylic acid for the treatment of inflammatory bowel disease." Gastroenterology 87: 480-481 (1984).
Dignass, A.U., et al., "Mesalamine Once Daily is More Effective Than Twice Daily in Patients With Quiescent Ulcerative Colitis." Clinical Gastroenterology and Hepatology 7:762-769 (2009).
Dipentum. (1998). In Physician's Desk Reference (52d ed., pp. 2264-2265).
Dipentum. (1999). In Physician's Desk Reference (53d ed., p. 2480).
Doelker, E., "Cellulose Derivatives.", Adv Polym Sci 107:199-265 (1993).
Dombal, F., "Ulcerative colitis: definition, historical background, aetiology, diagnosis, natural history and local complications." Postgrad. Med. J, 44:684-692 (1968).
Nielsen, O. "Kinetics of 5-aminosalicylic acid after jejunal installation in man," Br. J. Clin. Pharmac. 16:738-740 (1983).
Nokhodchi, A., et al, "Liquisolid Compacts: The Effect of Cosolvent and HPMC on Theophylline Release," Colloids & Surfaces B: Biointerfaces 79:262-269 (2010).
Nostrum W., et al, "Novel crosslinking methods to design hydrogels," Advanced Drug Delivery Reviews 54:13-36 (2002).
Nugent, S., et al, "Intestinal luminal pH in inflammatory bowel disease: possible determinants and implications for therapy with aminosalicylates and other drugs," Gut 48:571-577 (2001).
Oliveira, L. et al., "Maintaining remission in ulcerative colitis—role of once daily extended release mesalamine," Drug Design, Development and Therapy 5:111-116 (2011).
Omidian, H., et al., "Swelling agents and devices in oral drug delivery," J Drug Del Sci Tech 18(2):83-93 (2008).
Pantoprazole. (1999). In Therapeutic Drugs 2:11-14 (Dollery ed.).
Patchan, M., et al., "Synthesis and properties of regenerated cellulose-based hydrogels with high strength and transparency for potential use as an ocular bandage," Mat. Sci. Eng. C 33:3069-3076 (2013).
Pentasa. (1996). In Physician's Desk Reference (50d ed., p. 1527).
Pentasa. (1998). In Physician's Desk Reference (52nd ed., pp. 1229).
Pentasa. (1999). In Physician's Desk Reference (53rd ed., pp. 2630).
Peppas, N., et al., "Hydrogels in Pharmaceutical Formulations," Eur. J. Pharmaceutics Biopharmaceutics 50:27-46 (2000).
Peppas, N., et al., "A Simple Equation for Description of Solute Release I. Fickian and Non-Fickian Release from Non-Swellable Devices in the Form of Slabs, Spheres, Cylinders or Discs," J. Control Release 5:23-36 (1987).
Peppas, N., "Analysis of Fickian & Non-Fickian Drug Release from Polymers," Pharmaceutica Acta Helvetiae 60:110-111 (1985).
Poloxamer. (1994). In Handbook of Pharmaceutical Excipeints (2nd Wade ed., pp. 352-354).
Polymethacrylates. (1994). In Handbook of Pharmaceutical Excipeints (2nd Wade ed., pp. 363-365).
Porter, Stuart C., Key Factors in the Development of Modified-Release Pellets in Multiparticulate Oral Drug Delivery 217-284 (Ghebre-Sellassie ed. 1994).
Principles and Practice of Pharmaceutics. (1994). In The Pharmaceutical Codex (12th Ed., pp. 212-214).
Propranolol (hydrochloride). (1999). In Therapeutic Drugs, vol. 2: p. 259-264 (Dollery ed.).
Pygall, S. "Detailed microscopic visualization of hydration and swelling in a rapidly hydrating particle bed containing a cellulose ether," Gyms and Stabilizers for the Food Industry 14:41-46 (2008).
Rahman, M., et al, "Formulation and evaluation of Ranolazine sustained release matrix tablets using Eudragit and HPMC," Int J Pharm Biomed Res 2(1):7-12 (2011).

Rasmussen, S. et al., "5-Aminosalicylic Acid in a Slow-Release Preparation: Bioavailability, Plasma Level, and Excretion in Humans," Gastroenterology 83:1062-1070 (1982).
Reynolds, T., et al. "Polymer erosion and drug release characterization of hydroxypropyl methylcellulose matrices," Journal of Pharmaceutical Sciences 87(9):1115-1123 (1998).
Riley, S., et. al., "Tests of Renal Function in Patients with Quiescent Colitis: Effects of Drug Treatment," Gut 33 (10):1348-1352 (1992).
Ritger, P. & Peppas, N., "A Simple Equation for Description of Solute Release II. Fickian and Anomalous Release from Swellable Devices," J Control Release 5:37-42 (1987).
Rosiak, Janusz M. & Yoshii, Fumio, "Hydrogels and Their Medical Applications" Nuclear Instruments and Methods in Physics Res. 151:B 56 (1999).
Rubenstein, A. et al., "Gastrointestinal-physiological variables affecting the performance of oral sustained release dosage forms," in Oral Sustained Release Formulations: Design and Evaluation (Yacobi and Halperin-Walega Eds.) 125-156, (1988).
Safdi, Alan et al., Determination of 5-ASA in Whole or Partial Mesalamine Delayed-Release Tablets Recovered From Fecal Samples of Healthy Volunteers: Do 5-ASA Delivery Systems Matter in the Treatment of Ulcerative Colitis?, presented at American College of Gastroenterology Meeting (Oct. 28-Nov. 1, 2005).
Sandborn, W.J., et al., "Once-Daily Dosing of Delayed-Release Oral Mesalamine (400-mg Tablet) Is an Effective as Twice-Daily Dosing for Maintenance of Remission of Ulcerative Colitis," Gastroenterology, 138:1286-1296 (2010).
Shale, M.J. et al., "Studies of compliance and delayed-release mesalazine therapy in patients with inflammatory bowel disease," Alimentary Pharmacology & Therapeutics 18:191-198 (2003).
Siepmann, J. & Peppas, N., "Higuchi Equation: Derivation, Applications, use and Misuse," Int'l J. Pharm. 416:6-12 (2011).
Siepmann, J. & Siepmann, F., "Mathematical Modeling of Drug Delivery," Int J Pharm 364:328-343 (2008).
Siepmann, J., et al., "Modeling of drug release from delivery systems based on the hydroxypropyl methylcellulose," Advanced Drug Delivery Reviews 48:139-157 (2001).
Silva, S., et al., "Aggregation and gelation in hydroxypropylmethyl cellulose aqueous solutions," Journal of Colloid and Interface Science, 327:333-340 (2008).
Singh, B., "Modified-Release Solid Formulations for Colonic Delivery," Recent Patents on Drug Delivery & Formulation 1:53-63 (2007).
Sinha, A., et al., "Intestinal Performance of Two Mesalamine Formulations in Patients with Active Ulcerative Colitis as Assessed by Gamma Scintigraphy," Practical Gastroenterology pp. 56-69 (2003).
Stempel, E., "Prolonged Drug Action," in Husa's Pharmaceutical Dispensing 464 (Eric W. Martin & John E. Hoover eds., 6th ed. 1966).
Stolk, L. "Dissolution profiles of mesalazine formulations in vitro." Pharmaceutisch Weekblad Scientific Edition 12:200 (1990).
Tahara, K., et al, "Overall mechanism behind matrix sustained-release (SR) tablets prepared with hydroxypropyl methylcellulose 2910," J. Controlled Release 35:59-66 (1995).
Tiwari, S., et al, Modulation of drug release from hydrophilic matrices. Advancing process Solutions—Pharmaceutical Technology. Sep. 2008.
Topcare Lansoprazole PI (capsule delayed release) (Revised Sep. 2013).
Travis, S., et al., "Optimum dose of olsalazine for maintaining remission in ulcerative colitis," Gut 35:12821286 (1994).
Tu, J., et al., "Polymers in Oral Modified Release Systems," in Oral Controlled Release Formulation Design and Drug Delivery: Theory to Practice (ed. H. Wen, K. Park, Wiley, NY, p. 81, accessed on line Feb. 2014).
Tukaram, B., et.al., "The Effects of Lactose, Microcrystalline Cellulose and Dicalcium Phosphate on Swelling and Erosion of Compressed HPMC Matrix Tablets: Texture Analyzer," Iran J Pharm Res 9(4):349-358 (2010).
U.S. Pharmacopeial Convention, Section 1151 Pharmaceutical Dosage Forms, in USP 36-NF 31 854,861 (2014).
van Hees, P., et al., "Compliance to therapy in patients on a maintenance dose of sulfasalazine," Journal of Clinical Gastroenterology 4(4):333-336 (1982).

(56) References Cited

OTHER PUBLICATIONS

Wadworth, A. & Fitton, A., "Olsalazine: A Review of its Pharmacodynamic and Pharmacokinetic Properties, and Therapeutic Potential in Inflammatory Bowel Disease," Drug 41:647-664 (1991).
Wang, Pao-Li, et al., "Thermal-induced denaturation of two model proteins: effect of poloxamer 407 on solution stability," Int'l J. of Pharmaceutics 96:41-49 (1993).
Washington, Nina et al., "Drug Delivery to the Large Intestine and Rectum," Physiological Pharmaceutics, Barriers to Drug Absorption pp. 144-180 (2d ed. 2001).
Watts, P., et al., "Encapsulation of 5-aminosalicylic acid into Eudragit RS microspheres and modulation of their release characteristics by use of surfactants," Journal of Controlled Release 16:311-318 (1991).
Donald, I., et al., "The value of 5-aminosalicylic acid in inflammatory bowel disease for patients intolerant or allergic to sulphasalazine." Postgraduate Medical Journal 61:1047-1048 (1985).
Dow Brochure: Formulating for Controlled Release with Methocel Premium cellulose ethers (1995).
Dow Brochure: Using Dow Excipients for Controlled Release of Drugs in Hydrophilic Matrix Systems (2006).
Drug Release. (1990). In USP XXII: The United States Pharmacopeia (36th ed., pp. 1580-1583).
Dukic-Ott, A., et al., "Production of pellets via extrusion-spheronisation without the incorporation of microcrystalline cellulose: A critical review." European Journal of Pharmaceutics and Biopharmaceutics 71: 38-46 (2009).
EC-Naprosyn®/ Naprosyn®/ Anaprox®/Anaprox® DS / Naprosyn® product insert, (Revised Nov. 2004).
Efentakis, M. et al, "Dimensional changes, gel layer evolution and drug release studies in hydrophilic matrices." Int J Pharm 339: 66-75 (2007).
Erkoboni, David F., Extrusion-Spheronization as a Granulation Technique in Handbook of Pharmaceutical Granulation Technology 333-368 (Parikh ed., 1997).
Erythromycin. (1996). In The Merck Index (12 ed. pp. 3720-3721).
Erythromycin. (1999). In Therapeutic Drugs, 1: E50-54 (Dollery ed.).
Evans, D.F. et al., "Measurement of gastrointestinal pH profiles in normal ambulant human subjects." Gut 29:1035-1041 (1988).
FDA Approval Package for Pentasa Capsules (1993).
Feagan, B., "Oral 5-aminosalicylic maintenance of remission in ulcerative colitis (review)." The Cochrane Collaboration (2012).
Feagan, B.G. et al., "Are There Any Differences in the Efficacy and Safety of Different Formulations of Oral 5-ASA Used for Induction and Maintenance of Remission in Ulcerative Colitis? Evidence from Cochrane Reviews." Inflammatory Bowel Disease 19:2031-2040 (2013).
Fielden, K., et al., "Extrusion and Extruders" in Pharmaceutical Technology 5 (1992).
FIP Guidelines for Dissolution Testing of Solid Oral Products, Pharm Ind 57:362-369 (1995).
Food and Drug Administration. Guidance for Industry, SUPAC-MR: Modified Release Solid Oral Dosage Forms. Food and Drug Administration, Rockville, Md., Sep. 1997.
French, D., et al., "Evaluation of the Physicochemical Properties and Dissolution Characteristics of Mesalamine: Relevance to Controlled Intestinal Drug Delivery," Pharmaceutical Research 10:1285-1290 (1993).
Friedman, G., "Sulfasalazine and New Analogues," The American Journal of Gastroenterology 81:141-144 (1986).
Friend, D., "Colon-specific drug delivery" Advanced Drug Delivery Reviews 7:149-199 (1991).
Galeone, M. et al., "In vivo demonstration of delivery mechanisms from sustained-release pellets." Current Therapeutic Research 29:217-234 (1981).

Galichet, "Cellulose, Microcrystalline." In Handbook of Pharmaceutical Excipients 132 (5th Ed. 2006).
Ganji, F. et al., "Theoretical description of hydrogel swelling: A review." Iranian Polymer Journal 19:375-398 (2010).
Gardner, DJ et al., "Adhesion and Surface Issues in Cellulose and Nanocellulose." J Adhesion Sci Technol 22:545-567 (2008).
Ghebre-Sellassie, I., Chapter 1: Pellets: A General Overview, Pharmaceutical Pelletization Technology 1-13 (1989).
Ghebre-Sellassie, I., Chapter 10: Formulation Variables, Pharmaceutical Pelletization Technology 217-239 (1989).
Ghebre-Sellassie, I., Chapter 2: Conventional and Specialized Coating Pans, Pharmaceutical Pelletization Technology 15-38 (1989).
Ghebre-Sellassie, I., Chapter 4: Extrusion and Spheronization Equipment, Pharmaceutical Pelletization Technology 71-100 (1989).
Ghebre-Sellassie, I., Chapter 7: Solution and Suspension Layering. Pharmaceutical Pelletization Technology 145-164 (1989).
Ghebre-Sellassie, I., Chapter 9: Extrusion and Spheronization Technology, Pharmaceutical Pelletization Technology 187-216 (1989).
Grillet, A., et al., Polymer Gel Rheology and Adhesion. Rheology, Dr. Juan De Vicente (Ed.), ISBN: 978-953-51-0187-1. 2012.
Gruber, P., et al., "Some biological issues in oral, controlled drug delivery." Adv. Drug. Del. Rev. 1:1-18 (1987).
Guidance for Industry, SUPAC-MR: Modified Release Solid Oral Dosage Forms, Food and Drug Administration, Sep. 1997.
Guimaraes, M., et al., "Does Material Matter?" Endovascular Today 70-74 (2013).
Gulrez, S., et al., "Hydrogels: Methods of preparation, characterization and applications." In Progress in Molecular and Environmental Bioengineering—From Analysis and Modeling to Technology Applications 117-150 (2011).
Gurgel, L., et al.,Characterization of depolymerized residues from extremely low acid hydrolysis (ELA) of sugarcane bagasse cellulose: Effects of degree of polymerization, cystallinity and crystallize site on thermal decomposition. Ind. Crops Prod. 36: 560-571 (2012).
Hadgraft, J., et al., "Drug Release from Pluronic Gels," 34 (Supp) J. Pharm. Pharmacol. 3P (1982).
Hanauer, S., et al., "Mesalamine Capsules for Treatment of Active Ulcerative Colitis: Results of a Controlled Trial." American J. Gastroenterology 88:1188 (1993).
Harwood, R., "Hypermellose," in Handbook of Pharmaceutical Excipients (5th Ed. 346-349) (2006).
Hardy, J., Enteric Coatings and Delayed Release in Drug Delivery to the Gastrointestinal Tract 83-96 (Hardy ed. 1989).
Healey, J., "Gastrointestinal Transit and Release of Mesalazine Tablets in Patients with Inflammatory Bowel Disease." Scand J. Gastroenterology 25: 47-51 (1990).
Hoare, T. & Kohane, D., "Hydrogels in drug delivery: Progress and challenges," Polymer 49:1993-2007 (2008).
Hogan, J., "Some formulation factors involved in Hydroxypropyl Methylcellulose Controlled Release; Matrices," Excipients and delivery systems for pharmaceutical formulations—The Royal Society of Chemistry, pp. 186-190, 1995.
Watts, P., et al., "Colonic Drug Delivery," Drug Dev & Indus Pharm. 23(9):893-913 (1997).
Wilding, I., et al., "Targeting of Drugs and Vaccines to the Gut," Pharmac. Ther. 62:97-124 (1994).
Wilks, Samuel & Moxon, Walter, "Lectures on Pathological Anatomy." https://archive.org/stream/ lecturesonpatho00moxogoog#page/n431/mode/2up 1875, pp. 408-409.
Yu, D., et al., "Pharmacokinetics of 5-aminosalicylic Acid from Controlled-Release Capsules in Man," Eur. J. Clin. Pharmacol 48:273-277 (1995).

* cited by examiner

COMPOSITIONS AND METHODS FOR TREATMENT OF BOWEL DISEASES WITH GRANULATED MESALAMINE

CROSS-REFERENCE TO RELATED APPLICATIONS

This application is related to U.S. Provisional Patent Application Nos. 61/102,807 and 61/109,708; filed 3 Oct. 2008 and 30 Oct. 2008, respectively. These applications are incorporated herein by reference in their entirety.

BACKGROUND

Ulcerative colitis (UC) is an idiopathic, chronic relapsing and remitting, non-specific inflammatory disease of the colonic mucosa. Acute episodes are characterized by chronic diarrhea, rectal bleeding and abdominal pain. Stool volume correlates directly with disease severity, since the colon becomes increasingly unable to reabsorb water and electrolytes as inflammation of the mucosa increases. Loss of water and electrolytes can lead to dehydration, weight loss and serum electrolyte disturbances. Inflammation of the mucosa leads to erosions, which eventually result in rectal bleeding. Anemia and hypoalbuminemia often develop as the disease progresses. Muscosal Inflammation also leads to smooth muscle spasm that, in turn, causes urgency to defecate and tenesmus. Systemic manifestations include anorexia, weight loss, fatigue, fever, increased sedimentation rate, arthritis, eye inflammation, anxiety, tachycardia, and elevation in liver function tests (LFTs).

UC also has a profound emotional and social impact on the affected individual. The etiology and pathogenesis of UC are multifactorial and incompletely understood. One theory is that the disease results from inappropriate activation of the mucosal immune system, resulting in the inflammatory response. Theories regarding the inappropriate activation suggest a role for genetic predisposition and/or environment triggers.

UC is most commonly reported in Northern Europe and the United States; reported less frequently in the Middle East and the Southern Hemisphere; and infrequently seen in South America, Asia and Africa. The annual incidence rate is 10.4 to 12.0 cases per 100,000 people with a prevalence rate of 35 to 100 cases per 100,000 people. Although UC occurs at any age, the incidence peaks at 15 to 25 years and 55 to 65 years. The disease is 30% more predominant in females; and a higher incidence is associated with the Jewish population. The goal of treatment in UC is to induce and maintain remission, and improve quality of life.

Subjects with ulcerative colitis may experience periods of remission (times when the symptoms go away) that can last for months or years. However, most subjects' symptoms eventually return. Active therapy is treatment given to treat UC symptoms when they are active. Maintenance therapy refers to treatment given to subjects to enable them to stay in remission, to maintain their health in a disease-free, or limited-disease, state. Maintenance medications must be taken for a prolonged period of time.

The clinical efficacy of oral mesalamine compounds to treat UC has related to delivery of the intact molecule to the colonic mucosa without breakdown during digestion. Currently, oral mesalamine treatments are based on 3 types of delivery systems: (1) azo-bonded to release drug in the colon once the drug is exposed to colonic bacteria (Azulfidine, Dipentum® capsules (olsalazine), and balsalazide; (2) polymer coated (Asacol® mesalamine) delayed-release tablets) to provide a release of drug when the pH in the digestive tract reaches the desired value; and (3) time-dependent release mechanisms (Pentasa® capsules). Problems with other formulations include variation within formulations in the release of mesalamine, including premature release, the possibility of dose dumping, and sensitivity to conditions that increase gastric pH and cause premature release of mesalamine (e.g., ingestion of a meal).

Examples of mesalamine formulations may be found in U.S. Pat. Nos. 6,277,412; 6,551,620 and US Publication 2003/0133983.

Many subject's suffering from bowel diseases (BD), such as ulcerative colitis, diverticulitis, Crohn' s disease, and inflammatory bowel disease are not adequately controlled on currently available formulations of available medications.

SUMMARY

The present invention features compositions and related methods for treating gastrointestinal disorders, e.g., inflammatory gastrointestinal disorders, irritable bowel disease, gastrointestinal motility disorders, functional gastrointestinal disorders, gastroesophageal reflux disease (GERD), Crohn's disease, ulcerative colitis, and diverticulitis, inflammatory bowel disease, and gastroparesis, with a granulated mesalamine formulation.

In one aspect, provided herein are methods of treating a subject having a gastrointestinal disorder comprising administering to the subject an effective amount of a granulated mesalamine formulation; thereby treating the subject.

In one embodiment, a prior treatment of the subject with another formulation of mesalamine has failed.

In one embodiment, the gastrointestinal disorder is selected from the group consisting of: irritable bowel disease, gastrointestinal motility disorders, functional gastrointestinal disorders, gastroesophageal reflux disease (GERD), Crohn's disease, ulcerative colitis (UC), active UC, UC in remission, diverticular disease, inflammatory bowel disease, and gastroparesis.

In one embodiment, the effective amount of granulated mesalamine formulation comprises from between about 0.5 to about 4 g per day.

In one embodiment, the effective amount of granulated mesalamine formulation comprises about 1.5 g per day.

In one embodiment, the effective amount of granulated mesalamine formulation comprises about 3 g per day.

In one embodiment, the 1.5 g of granulated mesalamine formulation is administered as four 375 mg dosage units.

In one embodiment, the subject maintains remission of the gastrointestinal disease.

In one embodiment, the subject remains relapse free of the gastrointestinal disease.

In one embodiment, the granulated mesalamine formulation is administered as a single daily dosage.

In one aspect, provided herein are methods of treating a subject having ulcerative colitis (active or in remission) comprising, administering to the subject an effective amount of a granulated mesalamine formulation as a single daily dosage; thereby treating the subject.

In one embodiment, the subject maintains remission of ulcerative colitis.

In one embodiment, the subject remains relapse free of ulcerative colitis.

In one embodiment, the granulated mesalamine formulation is a delayed and extended release formulation.

In one embodiment, "delayed and extended" release formulations comprise formulations that first release mesalamine in the ileum and continue to release mesalamine throughout the terminal ileum and colon.

In one aspect, provided herein are methods of treating a subject having a gastrointestinal disorder comprising, determining treatment failure from a non-granulated 5-ASA mesalamine formulation; and responsive to such failure, administering to the subject an effective amount of a granulated mesalamine formulation; thereby treating the subject.

In one aspect, provided herein are methods of treating a subject having a gastrointestinal disorder comprising, administering to the subject an effective amount of a granulated mesalamine formulation, wherein treatment of the subject with another formulation of mesalamine has failed; thereby treating the subject.

In one aspect, provided herein are methods of treating a subject having a gastrointestinal disorder comprising administering to the subject an effective amount of a granulated mesalamine formulation orally, once daily, in the morning.

In one aspect, provided herein are methods of treating or maintaining remission of ulcerative colitis, comprising, administering from between about 0.75 g and about 4 g of a granulated mesalamine formulation orally to the subject once daily in the morning. In one embodiment, about 1.5 g of the granulated mesalamine formulation is administered. In one embodiment, about 3 g of the granulated mesalamine formulation is administered. In one embodiment, the granulated mesalamine formulation is taken without regard to meals. In one embodiment, the granulated mesalamine formulation is taken with or without food. In one embodiment, the granulated mesalamine formulation is not co-administered with antacids. In one embodiment, the 1.5 g of granulated mesalamine formulation comprises four capsules. In one embodiment, the four capsules each comprise 0.375 g mesalamine. In one embodiment, the four capsules each comprise from between about 0.25 g to about 0.45 g mesalamine.

In one embodiment, the methods further comprise an evaluation of renal function prior to administration of the granulated mesalamine formulation.

In one embodiment, treatment is contraindicated if a subject has hypersensitivity to salicylates or aminosalicylates.

In one embodiment, the granulated mesalamine formulation is a locally-acting aminosalicylate.

In one embodiment, the granulated mesalamine formulation is an extended release formulation.

In one embodiment, "extended release" comprises release throughout the lumen of a colon.

In one embodiment, delayed release comprises release at between about pH 5.7 to about pH 7.

In one embodiment, delayed release comprises release at about pH 6.

In one embodiment, treatment of the subject with another formulation of mesalamine has failed.

In one embodiment, the subject remains relapse free.

Provided herein is a locally-acting aminosalicylate (e.g., a granulated mesalamine formulation) indicated for the maintenance of remission of ulcerative colitis in a subject, for example humans. In one embodiment, the subject is an adult human. In other embodiments, the subject is a juvenile or child human. In one embodiment, a granulated mesalamine formulation is administered for the maintenance of remission of ulcerative colitis in subjects 18 years of age and older.

In one embodiment, four capsules of the granulated mesalamine formulation are administered once daily (e.g., 1.5 g/day) in the morning, afternoon or evening with or without food. In one preferred embodiment, the capsules of the granulated mesalamine formulation are administered once daily (e.g., 1.5 g/day) in the morning, with or without food. In one embodiment, the granulated mesalamine formulation is not administered with antacids.

Because the dissolution of the coating of the granulated mesalamine formulation, the dissolution of the formulation depends on pH.

In one embodiment, the granulated mesalamine formulation is administered as extended-release capsules 0.375 g each. In one embodiment, the dose for maintenance of remission of ulcerative colitis in adult subjects comprises 1.5 g (four granulated mesalamine formulation) orally once daily in the morning without regard to meals.

In certain embodiment, subject with hypersensitivity to salicylates, aminosalicylates, or any component of the granulated mesalamine formulation should not be administered the granulated mesalamine formulation.

In certain embodiments, the subject is advised that when being administered granulated mesalamine formulation renal impairment may occur. In one embodiment, the subject's renal function is assessed at the beginning of treatment. In one embodiment, renal function is assessed before initiating therapy with mesalamine. In other embodiments, subject's renal function is assessed periodically during therapy. In certain embodiments, the subject is advised that acute exacerbation of colitis symptoms can occur. In certain embodiments, the subject is advised that the granulated mesalamine formulation should be used with caution in subjects with renal disease. In certain embodiments, the blood cell counts are monitored in geriatric subjects being administered the granulated mesalamine formulation. In certain embodiments, the subject is advised that the granulated mesalamine formulation contains aspartame.

In certain embodiments, the subject is advised that the granulated mesalamine formulation should be used with caution with pre-existing liver disease.

In one embodiment, the subject is advised that there are adverse reactions associated with administration of the granulated mesalamine formulation. In one embodiment, the adverse reactions include, for example, (incidence ≥3%) are headache, diarrhea, upper abdominal pain, nausea, nasopharyngitis, flu or flu-like illness, sinusitis. In one embodiment, the granulated mesalamine formulation comprises extended-release capsules containing 0.375 g mesalamine. In one embodiment, the granulated mesalamine formulation comprises delayed and extended-release capsules containing 0.375 g mesalamine.

In one embodiment, the subject is advised that mesalamine has been associated with an acute intolerance syndrome that may be difficult to distinguish from a flare of inflammatory bowel disease. Symptoms include, for example, cramping, acute abdominal pain and bloody diarrhea, sometimes fever, headache, and rash. In one embodiment, if acute intolerance syndrome is suspected, the subject is advised to promptly discontinue treatment with the granulated mesalamine formulation.

In one embodiment, the subject is advised that subjects who have experienced a hypersensitivity reaction to sulfasalazine may have a similar reaction to the granulated mesalamine formulation.

In another embodiment, the subject is advised that based on in vitro studies, granulated mesalamine formulation is not expected to inhibit the metabolism of drugs that are substrates of CYP1A2, CYP2C9, CYP2C19, CYP2D6, or CYP3A4.

In one embodiment, the subject is advised that low concentrations of mesalamine and higher concentrations of its N-acetyl metabolite have been detected in human breast milk.

In another embodiment, the subject is advised that the clinical studies of granulated mesalamine formulation did not include sufficient numbers of subjects aged 65 and over to determine whether they respond differently than younger subjects. In another embodiment, the subject is advised that the greater frequency of decreased hepatic, renal, or cardiac function, and of concomitant disease or other drug therapy in elderly subjects should be considered when prescribing granulated mesalamine formulation.

In another embodiment, the subject is advised that a higher incidence of blood dyscrasias, i.e., neutropenia, pancytopenia, in subjects who were 65 years or older who were taking mesalamine-containing products. In one embodiment, the subject is advised that caution should be taken to closely monitor blood cell counts during mesalamine therapy.

In another embodiment, the subject is advised that reproduction studies with mesalamine have been performed in rats and rabbits and have revealed no evidence of impaired fertility or harm to the fetus due to mesalamine.

In one embodiment, the subject is advised that there is no specific antidotes for mesalamine overdose; however, therapy for salicylate toxicity may be beneficial in the event of acute overdosage. This includes prevention of further gastrointestinal tract absorption by emesis and, if necessary, by gastric lavage. Fluid and electrolyte imbalance should be corrected by the administration of appropriate intravenous therapy. Adequate renal function should be maintained.

In one embodiment, the subject and/or the healthcare provider is advised that granulated mesalamine formulation is a pH dependent delayed-release product and this factor should be considered when treating a suspected overdose.

In one embodiment, the granulated mesalamine formulation comprises a capsule comprising a delayed- and extended-release dosage form for oral administration. In one embodiment, each capsule comprises 0.375 g of mesalamine USP (5-aminosalicylic acid, 5-ASA), an anti-inflammatory drug.

In one embodiment, the subject and/or the healthcare provider is advised not to take granulated mesalamine formulation capsules with antacids, because it could affect the way granulated mesalamine formulation dissolves.

In one embodiment, the subject is advised to contact a health care provider if they experience a worsening of ulcerative colitis symptoms, because it could be due to a reaction to granulated mesalamine formulation.

As used herein, renal impairment, includes minimal change nephropathy, acute and chronic interstitial nephritis, and, rarely, renal failure.

As used herein, salicylate toxicity symptoms includes for example, hematemesis, tachypnea, hyperpnea, tinnitus, deafness, lethargy, seizures, confusion, or dyspnea. Severe intoxication may lead to electrolyte and blood pH imbalance and potentially to other organ (e.g., renal and liver) involvement.

In another embodiment, the invention provides methods of administering granulated mesalamine as a treatment for a gastrointestinal disorder, by advising a health care worker and/or a subject that subjects previously prescribed corticosteroids followed by granulated mesalamine have a decreased incidence of adverse events; and administering the granulated mesalamine to the patient in order to treat the gastrointestinal disorder.

In related embodiments, the gastrointestinal disorder is ulcerative colitis. In another related embodiment, the adverse events are ulcerative colitis-related adverse events.

In another embodiment, the invention provides methods of decreasing the incidence of adverse events in the subject having a gastrointestinal disorder after the subject has been treated with corticosteroids, by administering granulated mesalamine to the subject, thereby decreasing the incidence of adverse events.

In related embodiments, the gastrointestinal disorder is ulcerative colitis. In another related embodiment, the adverse events are ulcerative colitis-related adverse events.

In a related embodiment, the subject is administered a once daily dose of granulated mesalamine.

In one embodiment, the once daily does is 1.5 g of granulated mesalamine and can be administered as, for example, four capsules of 375 mg granulated mesalamine.

In another embodiment, the invention provides methods of treating a subject having a gastrointestinal disorder, by advising a health care worker and/or a subject that subjects having a low mucosal score are most likely remain in remission from the gastrointestinal disorder; and administering the granulated mesalamine to the patient in order to treat the gastrointestinal disorder.

In related embodiments, the gastrointestinal disorder is ulcerative colitis. In another related embodiment, the low mucosal score is 0.

Other aspects and embodiments are disclosed infra.

BRIEF DESCRIPTION OF THE DRAWINGS

In FIG. 2A, the primary efficacy analysis, patients were counted as treatment failures only if they withdrew for lack of efficacy or an ulcerative colitis-related adverse event. In FIG. 2B, patients withdrawing for any reason were counted as treatment failures.

DETAILED DESCRIPTION

Figure 1:
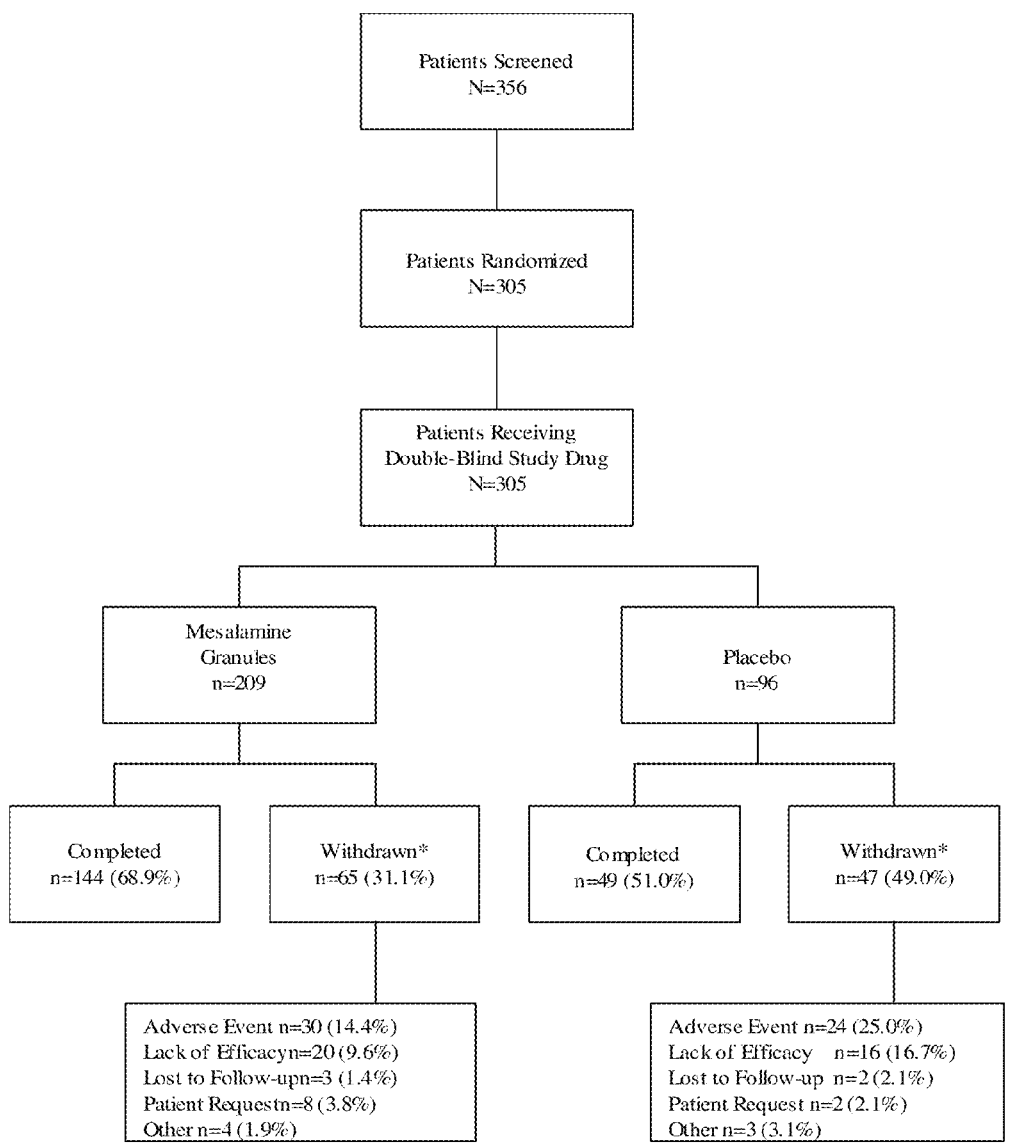
FIG. 1 is a flow chart depicting patient disposition.

It is to be understood that both the foregoing general description and the following detailed description are exemplary and explanatory only and are not restrictive of the invention as claimed.

As discussed below in the Examples, in two randomized, double-blind, placebo-controlled, phase 3 studies, more granulated mesalamine (GM) treated patients than placebo-treated patients remained relapse-free for 6 months (79% versus 62%; p<0.001) and GM reduced the risk of developing UC by 52% (hazard ratio for the risk of relapse in the GM group relative to the placebo group was 0.48 (95% CI 0.35, 0.66). This analysis investigated the potential effect of prognostic factors contributing to UC relapse on maintenance of response to GM.

Also, in two independent, randomized, double-blind, placebo-controlled trials, patients with documented UC remission (revised Sutherland Disease Activity Index [DAI] subscores: rectal bleeding 0; mucosal appearance <2) were randomized 2:1 to receive 1.5 g granulated mesalamine in capsules, or a placebo, once daily for 6 months. The primary efficacy endpoint was the proportion of patients who remained relapse free after 6 months of treatment (relapse defined as a rectal bleeding subscore ≥1 and a mucosal appearance subscore ≥2 per DAI; UC flare or UC symptoms leading to withdrawal; or initiated medication used to treat UC). Prognostic factors for maintenance of remission included baseline demographics and disease characteristics including: age; sex; DAI total score, and sub scores for stool frequency, mucosal appearance, physician's assessment; corticosteroid pretreatment; time to last flare; and disease duration, and were evaluated by covariate analysis.

Demographics and baseline characteristics were similar between groups (n=373 GM, n=189 placebo). Independent predictors of relapse included DAI score (p=0.0217), stool frequency subscore (p=0.0106), mucosal appearance score (p=0.0007), physician's global UC assessment score (p=0.0136), country (p=0.0018), and 5-ASA pretreatment (p=0.0066). After controlling for these prognostic factors, GM dosed at 1.5 g once daily significantly reduced the risk of relapse by 52% versus placebo (odds ratio, 0.48; 95% CI, 0.322-0.711; p=0.0003). The most influential prognostic factors for maintenance of remission in this covariate analysis were the DAI mucosal subscore (p=0.0014).

In addition, it was discovered that 1.5 g granulated mesalamine taken once-daily was clinically demonstrated to be more effective than placebo in maintaining long-term remission of UC (79 percent vs. 58 percent of subjects were relapse-free at six months [P<0.001]). A larger proportion of granulated mesalamine subjects showed a clinically favorable change from baseline in physician-rated disease activity at month six compared with placebo (78 percent vs. 64 percent [P=0.005]). Subjects taking granulated mesalamine also had a higher probability of remaining relapse-free at six months (77 percent vs. 56 percent [P<0.001]).

An additional study showed that the pharmacokinetic profile and systemic absorption of mesalamine granules was comparable whether administered once- or twice-daily. In addition, the overall systemic absorption of mesalamine granules was low and essentially unaltered by a high-fat meal eaten before dosing, as seen in another study. The ability to take mesalamine granules with or without food, along with its once-daily dosing, may improve patient compliance and treatment success.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The term "administration" or "administering" includes routes of introducing a granulated mesalamine formulation to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, eye drops, ointment, suppository, etc administration by injection, infusion or inhalation; topical by lotion or ointment; and rectal by suppositories. The injection can be bolus or can be continuous infusion. Depending on the route of administration, a granulated mesalamine formulation can be coated with or disposed in a selected material to protect it from natural conditions that may detrimentally affect its ability to perform its intended function. A granulated mesalamine formulation can be administered alone, or in conjunction with either another agent or agents as described above or with a pharmaceutically-acceptable carrier, or both. A granulated mesalamine formulation can be administered prior to the administration of the other agent, simultaneously with the agent, or after the administration of the agent. Furthermore, a granulated mesalamine formulation can also be administered in a proform, which is converted into its active metabolite, or more active metabolite in vivo.

Administration "in combination with" one or more further therapeutic agents includes simultaneous (concurrent) and consecutive administration in any order.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, polyethylene glycol (PEG).

The term "effective amount" includes an amount effective, at dosages and for periods of time necessary, to achieve the desired result, e.g., sufficient to treat or prevent UC or other mesalamine related disorders in a patient or subject. An effective amount of a granulated mesalamine formulation may vary according to factors such as the disease state, age, and weight of the subject, and the ability of a granulated mesalamine formulation to elicit a desired response in the subject. Dosage regimens may be adjusted to provide the optimum therapeutic response. An effective amount is also one in which any toxic or detrimental effects (e.g., side effects) of a granulated mesalamine formulation are outweighed by the therapeutically beneficial effects.

"Ameliorate," "amelioration," "improvement" or the like refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between about any two of these values. Such improvement or change may be observed in treated subjects as compared to subjects not treated with granulated mesalamine, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of UC in a subject.

Amelioration may be transient, prolonged or permanent or it may be variable at relevant times during or after a granulated mesalamine formulation is administered to a subject or is used in an assay or other method described herein or a cited reference, e.g., within timeframes described infra, or about 1 hour after the administration or use of a granulated mesalamine formulation to about 28 days, or 1, 3, 6, 9 months or more after a subject(s) has received such treatment.

As used herein, "subject" includes organisms which are capable of suffering from a bowel disease or other disease treatable by granulated mesalamine or who could otherwise benefit from the administration of a granulated mesalamine as described herein, such as human and non-human animals. Preferred human animals include human subjects. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc. Susceptible to a bowel disease is meant to include subjects at risk of developing a bowel disease.

In one embodiment, the granulated mesalamine formulation disclosed herein and used in the methods described herein may be formulated to release more (in comparison to Asacol® and other formulations of mesalamine) of the active agent, mesalamine, directly to the therapeutic site of action (e.g., terminal ileum and colon) over a more prolonged period, and to decrease systemic availability relative to unencapsulated mesalamine granules. In one embodiment, the mesalamine is released over approximately 7 hours.

The granulated mesalamine formulation, for example in one embodiment, comprises a hard gelatin capsule shell containing a granulated mesalamine formulation which comprises, for example, an inner polymer matrix mesalamine core that is surrounded by an outer flavor coating, a middle coating, and an inner enteric pH dependent (delayed) release coating. The inner coating dissolves, for example, at pH≥6, but resists dissolution in the stomach, where gastric fluid is pH 1 during fasting and approximately pH 4 during a meal.

In one embodiment, following dissolution of the inner coating, the polymer matrix core of the granulated mesalamine provides a mechanism by which mesalamine, the active therapeutic ingredient, is uniformly and slowly released and distributed in the lumen of the colon. The release profile and additional pharmacokinetic data show that the pellets of the granulated mesalamine formulation have a relatively low rate and extent of systemic absorption, and that 85% to 90% of drug reaches the diseased area.

The direct and prolonged targeted release of the active agent from a granulated mesalamine formulation in UC subjects makes the formulation particularly effective as a once daily (QD) dosage regimen.

Relapse or treatment failure, as used herein, included a rectal bleeding score of 1 or more as described in the Sutherland DAI and a mucosal appearance score of 2 or more as described in the Sutherland DAI.

Article of Manufacture

Another embodiment includes articles of manufacture that comprise, for example, a container holding a pharmaceutical composition suitable for oral administration of granulated mesalamine in combination with printed labeling instructions providing a discussion of when a particular dosage form should be administered if the patient has previously failed treatment for a gastrointestinal disorder, such as ulcerative colitis. The dosage can be modified for administration to a subject suffering from ulcerative colitis, or include labeling for administration to a subject suffering from ulcerative colitis. Exemplary dosage forms and administration protocols are described infra. The composition will be contained in any suitable container capable of holding and dispensing the dosage form and which will not significantly interact with the composition and will further be in physical relation with the appropriate labeling. The labeling instructions may be consistent with the methods of treatment as described hereinbefore. The labeling may be associated with the container by any means that maintain a physical proximity of the two, by way of non-limiting example, they may both be contained in a packaging material such as a box or plastic shrink wrap or may be associated with the instructions being bonded to the container such as with glue that does not obscure the labeling instructions or other bonding or holding means.

Another aspect is an article of manufacture that comprises a container containing a pharmaceutical composition comprising granulated mesalamine wherein the container holds preferably granulated mesalamine compositions in unit dosage form and is associated with printed labeling instructions advising that administration of the granulated mesalamine may increase time to remission or relapse of ulcerative colitis.

In one embodiment, the instructions will inform or advise the prescribing physician, a pharmacist, or a subject that they should determine if the subject has previously failed treatment for ulcerative colitis or other gastrointestinal disorders before prescribing granulated mesalamine to treat ulcerative colitis in the subject. In another embodiment, the instructions will inform the subject and/or the healthcare provider that there is an extended time to remission or relapse of subjects that take granulated mesalamine in comparison to placebos.

Packaged compositions are also provided, and may comprise a therapeutically effective amount of granulated mesalamine capsules. Kits are also provided herein, for example, kits for treating gastrointestinal diseases in a subject. The kits may contain, for example, granulated mesalamine capsules and instructions for use when treating a subject for an ulcerative colitis disorder who has previously failed using mesalamine treatment. The instructions for use may contain prescribing information, dosage information, storage information, and the like.

Granulated Mesalamine Formulation

Mesalamine formulations are described in U.S. Pat. No. 6,277,412; 6,551,620 and US Publication 2003/0133983 to Dr. Falk Pharma GmbH. The entire contents of U.S. Pat. Nos. 6,277,412, 6,551,620 and US Publication 2003/0133983 are expressly incorporated by reference herein.

In one embodiment, the granulated mesalamine formulation comprises, for example, mesalamine, aspartame, citric acid, colloidal silicone dioxide, magnesium stearate, microcrystalline cellulose, povidone, simethicone emulsion, talc, titanium dioxide, triethyl citrate, vanilla flavoring, poly (methacrylic acid, methylmethacrylate) 1:1, poly(ethylacrylate-methylmethacrylate), and hypromellose. In one embodiment, the encapsulated granulated mesalamine formulation are subsequently encapsulated in capsules, for example, hard gelatin, size "00" capsule shells.

In one embodiment, each granulated mesalamine formulation capsule contains, for example, granules composed of mesalamine in a polymer matrix with an enteric coating that dissolves at pH 6 and above. Inactive ingredients of granulated mesalamine formulation capsules, may include one or more of, for example, colloidal silicon dioxide, magnesium stearate, microcrystalline cellulose, simethicone emulsion ethylacrylate/methylmethacrylate copolymer nonoxynol 100 dispersion, hypromellose, methacrylic acid copolymer, talc, titanium dioxide, triethyl citrate, aspartame, anhydrous citric acid, povidone, vanilla flavor, and edible black ink.

According to the methods described herein, the composition of granulated mesalamine formulations may be contained in a hard-shell capsule, which is a delayed and extended release dosage form for oral administration. Each capsule may contain, for example, 0.375 g of mesalamine USP (5-aminosalicylic acid, 5-ASA), an anti-inflammatory drug. The structural formula of mesalamine is:

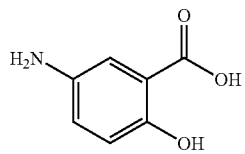

Molecular Weight: 153.135
Molecular Formula: $C_7H_7NO_3$

Formulations of granulated mesalamine useful in the methods disclosed herein comprise, for example, granulated mesalamine with a pH dependant coating that dissolves at pH 6 or greater, reached in the terminal ileum and colon, and a polymer matrix core which distributes the mesalamine slowly and uniformly throughout the lumen of the terminal ileum and colon. Thus, the formulation is, for example, delayed because it does not release the mesalamine until the terminal ileum and it is also extended release because it continuously releases mesalamine throughout the terminal ileum and the colon. This release profile is particularly advantageous to treat bowel diseases such as uncreative colitis, Crohn's disease and diverticulitis.

The formulation may also contain inactive ingredients, for example, capsules comprising, for example, colloidal silicon dioxide, magnesium stearate, microcrystalline cellulose, dry substance of simethicone emulsion 30%, dry substance of poly(ethylacrylatemethylmethacrylate) 2% nonoxynol 100 dispersion (Eudragit NE40D), hypromellose, poly(methacrylic acid, methylmethacrylate) 1:1 (Eudragit L100), talc, titanium dioxide, triethyl citrate, aspartame, anhydrous citric acid, povidone (K25), vanilla flavoring agent, and edible black ink.

The mechanism of action of 5-ASA is unknown, and without wishing to be bound by any particular scientific theory, it appears to be local to the intestinal mucosa rather than systemic. Mucosal production of arachidonic acid metabolites, both through the cyclooxygenase pathways, e.g., prostanoids, and through the lipoxygenase pathways, e.g., leukotrienes and hydroxyeicosatetraenoic acids, is increased in subjects with chronic inflammatory bowel disease, and it is possible that 5-ASA diminishes inflammation by blocking production of arachidonic acid metabolites.

Methods of Treatment

Described herein are methods of treating subjects suffering from or susceptible to gastrointestinal disorders by administering a granulated mesalamine formulation to a subject. The administration of a granulated mesalamine formulation, as described herein increases the efficacy of treatment in subjects having gastrointestinal disorders. This includes both active disease and prevention of relapse or maintenance of remission of disease, for example, active UC or UC in remission. Exemplary gastrointestinal disorders that may be treated using the methods of the invention include, but are not limited to, inflammatory gastrointestinal disorders such as irritable bowel disease, gastrointestinal motility disorders, functional gastrointestinal disorders, gastroesophageal reflux disease (GERD), Crohn's disease, ulcerative colitis, and diriticulitis, inflammatory bowel disease, and gastroparesis.

Therapeutically effective amounts, according to the methods described herein include doses from between about 0.5 g to about 4 g/day or from between about 1 g to about 3 g/day, specifically about 1.5 g/day or 3 g/day, of mesalamine formulation. Therapeutically effective amounts and dosage regimens include, administering four tablets, capsules, or granules of the formulation once each day, wherein each tablet, capsule, or granule (e.g., loose or in a sachet) comprises about 375 mg of mesalamine. For example, 1.5 g of a mesalamine in a granulated mesalamine formulation is administered as four capsules which contain granulated mesalamine formulation granules.

Yet another aspect of this invention relates to a method of treating a subject with a granulated mesalamine formulation who is in need thereof. Identifying a subject in need of such treatment can be in the judgment of a subject or a health care professional and can be subjective (e.g., opinion) or objective (e.g., measurable by a test or diagnostic method). In specific embodiments, the invention relates to identifying subjects in need of treatment with a granulated mesalamine formulation by identifying subjects who have previously had and failed treatment with another mesalamine formulation.

As used herein, a therapeutically effective amount means an amount effective, when administered to a human or non-human subject, to provide a therapeutic benefit such as an amelioration of symptoms, e.g., an amount effective to decrease the symptoms of ulcerative colitis or to maintain the remission of ulcerative colitis in a subject. In specific embodiments, a granulated mesalamine formulation may be administered once daily to a subject.

Dosages, according to certain preferred embodiments, range from between about 1 g to about 4 g of a granulated mesalamine formulation administered daily. Specifically, dosages of about 1.5 g/day or 3 g/day of a granulated mesalamine formulation are exemplified in the examples presented herein. Other appropriate dosages for methods according to this invention may be determined by health care professionals or by the subject. The amount of a granulated mesalamine formulation administered daily may be increased or decreased based on the weight, age, health, sex or medical condition of the subject. One of skill in the art would be able to determine the proper dose for a subject based on this disclosure.

The amount of the granulated mesalamine formulation of the invention which will be effective in the treatment of a particular disorder or condition will depend on the nature of the disorder or condition, and can be determined by standard clinical techniques. The precise dose to be employed in the formulation will also depend on the route of administration, and the seriousness of the disease or disorder, and should be decided according to the judgment of the practitioner and each subject's circumstances.

The total daily dosage of a granulated mesalamine formulation can range from about 1 g to about 4 g per day. For example, in general, the total daily adult dosage of a granulated mesalamine formulation of the present invention ranges from about 0.75 g to about 2 g, or any whole number or fractional amount in between. A single capsule or tablet may be formulated to contain about 250, 275, 375, 450, 525, 550, 575, 750, 800 or 1000 mg of a granulated mesalamine formulation. In one embodiment, a single capsule or tablet contains about 375 mg of a granulated mesalamine.

In an embodiment, a granulated mesalamine formulation is administered to the subject using a pharmaceutically-acceptable formulation. In one embodiment, a patient is administered granulated mesalamine as described in U.S. Pat. Nos. 6,277,412; 6,551,620 or US Publication 2003/0133983, but wherein the granulated mesalamine is advantageously in a capsule dosage form. For example, the granulated mesalamine formulation may be an extended-release capsule, containing, for example 0.375 g of mesalamine. The granulated mesalamine formulation may be a delayed and an extended-release formulation in capsules, containing, for example 0.375 g of mesalamine.

In one embodiment, the granulated mesalamine formulation is a locally-acting aminosalicylate. In another embodiment, the granulated mesalamine formulation maintains the remission of ulcerative colitis. The maintenance of remission is, for example, in adults and children. Adult, as used herein, includes, for example, subjects 18 years of age and older. The granulated mesalamine formulation may also be administered to treat active ulcerative colitis. In one embodiment, the granulated mesalamine formulation is administered until active symptoms are alleviated. In another embodiment, the granulated mesalamine formulation is administered during active disease and is continued to maintain remission.

In one embodiment, the granulated mesalamine formulation comprises four units of a dosage form (e.g., pills, capsules, tablets, sachets, granules) taken once daily. The once daily, could be, for example, in the morning, in the afternoon, in the evening or in the night.

In one embodiment, morning comprises, for example, between about 3 AM to about noon. Morning may also be, for example, the time after waking from sleep until noon.

In one embodiment, afternoon comprises, for example, between about noon to about 6 PM. Afternoon may also be, for example, the time from lunch until about 6 pm.

In one embodiment, evening comprises, for example, between about 6 PM to about 3 AM. Evening may also be, for example, the time from dinner starting to sleep.

In one embodiment, night comprises, for example, between about 8 PM to about 4 AM. Night may also be, for example, the time during which the sun has gone down and it is dark outside.

In one embodiment, the granulated mesalamine formulation may be taken without regard to food. For example, it may be taken with or without food.

For example, in one embodiment, the granulated mesalamine formulation may not be co-administered with antacids. It may be advantageous to not take the granulated mesalamine formulation with antacids because it could affect the way granulated mesalamine formulation dissolves.

In another embodiment, 1.5 g of a granulated mesalamine formulation is administered once daily in the morning.

In a further embodiment, 1.5 g of a granulated mesalamine formulation is administered once daily in the morning with or without food. For example, the granulated mesalamine formulation may be taken before, after, or during food consumption. The granulated mesalamine formulation may be taken, for example, on an empty or full stomach.

In yet another embodiment, 1.5 g of a granulated mesalamine formulation is administered once daily in the morning with or without food without antacids.

EXAMPLES

It should be appreciated that the invention should not be construed to be limited to the examples that are now described; rather, the invention should be construed to include any and all applications provided herein and all equivalent variations within the skill of the ordinary artisan.

Example 1

Pharmacokinetics

Absorption

The pharmacokinetics of 5-ASA and its metabolite, N-acetyl-5-aminosalicylic acid (N—Ac-5-ASA), were studied after a single and multiple oral doses of 1.5 g granulated mesalamine formulation in a crossover study in healthy subjects under fasting conditions. In the multiple-dose period, each subject received four capsules of 0.375 g granulated mesalamine (1.5 g total) every 24 hours (QD) for 7 consecutive days. Steady state was reached on Day 6 of QD dosing based on trough concentrations.

After single and multiple doses of granulated mesalamine formulation, peak plasma concentrations were observed at about 4 hours post dose. At steady state, moderate increases (1.5-fold and 1.7-fold) in systemic exposure ($AUC_{0-24}$) to 5-ASA and N—Ac-5-ASA were observed when compared with a single-dose of granulated mesalamine formulation.

Pharmacokinetic parameters after a single dose of 1.5 g granulated mesalamine formulation and at steady state in healthy subjects under fasting condition are shown in Table 1.

TABLE 1

Single Dose and Multiple Dose Mean (±SD) Plasma Pharmacokinetic Parameters of Mesalamine (5-ASA) and N-Ac-5-ASA after 1.5 g granulated mesalamine formulation Administration in Healthy Subjects

|  | Single Dose (n = 24) | Multiple Dose[c] (n = 24) |
|---|---|---|
| Mesalamine (5-ASA) | | |
| $AUC_{0-24}$ (μg * h/mL) | 11 ± 5 | 17 ± 6 |
| $AUC_{0-inf}$ (μg * h/mL) | 14 ± 5 | — |
| $C_{max}$ (μg/mL) | 2.1 ± 1.1 | 2.7 ± 1.1 |
| $T_{max}$ (h)[a] | 4 (2, 16) | 4 (2, 8) |
| $t_{1/2}$ (h)[b] | 9 ± 7 | 10 ± 8 |
| N-Ac-5-ASA | | |
| $AUC_{0-24}$ (μg * h/mL) | 26 ± 6 | 37 ± 9 |
| $AUC_{0-inf}$ (μg * h/mL) | 51 ± 23 | — |
| $C_{max}$ (μg/mL) | 2.8 ± 0.8 | 3.4 ± 0.9 |
| $T_{max}$ (h)[a] | 4 (4, 12) | 5 (2, 8) |
| $t_{1/2}$ (h)[b] | 12 ± 11 | 14 ± 10 |

[a]Median (range);
[b]Harmonic mean (pseudo SD);
[c]after 7 days of treatment

In a separate study (n=30), it was observed that under fasting conditions about 32%±11% (mean±SD) of the administered dose was systemically absorbed based on the combined cumulative urinary excretion of 5-ASA and N—Ac-5-ASA over 96 hours post-dose.

The effect of a high fat meal intake on absorption of mesalamine granules (the same granules contained in granulated mesalamine formulation capsules) was evaluated in 30 healthy subjects. Subjects received 1.6 g of mesalamine granules in sachet (2×0.8 g) following an overnight fast or a high-fat meal in a crossover study. Under fed conditions, $t_{max}$ for both 5-ASA and N—Ac-5-ASA was prolonged by 4 and 2 hours, respectively. A high fat meal did not affect $C_{max}$ for 5-ASA, but a 27% increase in the cumulative urinary excretion of 5-ASA was observed with a high fat meal. The overall extent of absorption of N—Ac-5-ASA was not affected by a high fat meal. As granulated mesalamine formulation and mesalamine granules in sachet were bioequivalent, granulated mesalamine formulation can be taken without regard to food.

Distribution

In an in vitro study, at 2.5 μg/mL, mesalamine and N—Ac-5-ASA are 43±6% and 78±1% bound, respectively, to plasma proteins. Protein binding of N—Ac-5-ASA does not appear to be concentration dependent at concentrations ranging from 1 to 10 μg/mL.

Metabolism

The major metabolite of mesalamine is N-acetyl-5-aminosalicylic acid (N—Ac-5-ASA). It is formed by N-acetyltransferase activity in the liver and intestinal mucosa.

Elimination

Following single and multiple doses of granulated mesalamine formulation, the mean half-lives were 9 to 10 hours for 5-ASA, and 12 to 14 hours for N—Ac-5-ASA. Of the approximately 32% of the dose absorbed, about 2% of the dose was excreted unchanged in the urine, compared with about 30% of the dose excreted as N—Ac-5-ASA.

In Vitro Drug-Drug Interaction Study

In an in vitro study using human liver microsomes, 5-ASA and its metabolite, N—Ac-5-ASA, were shown not to inhibit the major CYP enzymes evaluated (CYP1A2, CYP2C9, CYP2C19, CYP2D6, and CYP3A4). Therefore, mesalamine and its metabolite are not expected to inhibit the metabolism of other drugs that are substrates of CYP1A2, CYP2C9, CYP2C19, CYP2D6, or CYP3A4.

Carcinogenesis, Mutagenesis, Impairment of Fertility

Dietary mesalamine was not carcinogenic in rats at doses as high as 480 mg/kg/day, or in mice at 2000 mg/kg/day. These doses are about 2.6 and 5.4 times the recommended human dose of granulated mesalamine capsules of 1.5 g/day (30 mg/kg if 50 kg body weight assumed or 1110 mg/m$^2$), respectively, based on body surface area. Mesalamine was negative in the Ames test, the mouse lymphoma cell (L5178Y/TK+/−) forward mutation test, the sister chromatid exchange assay in the Chinese hamster bone marrow test, and the mouse bone marrow micronucleus test. Mesalamine at oral doses up to 320 mg/kg (about 1.7 times the recommended human dose based on body surface area) was found to have no effect on fertility or reproductive performance in rats.

Animal Toxicology and/or Pharmacology

Renal Toxicity

Animal studies with mesalamine (13-week and 26-week oral toxicity studies in rats, and 26-week and 52-week oral toxicity studies in dogs) have shown the kidney to be the major target organ of mesalamine toxicity. Oral doses of 40 mg/kg/day (about 0.20 times the human dose, on the basis of body surface area) produced minimal to slight tubular injury, and doses of 160 mg/kg/day (about 0.90 times the human dose, on the basis of body surface area) or higher in rats produced renal lesions including tubular degeneration, tubular mineralization, and papillary necrosis. Oral doses of 60 mg/kg/day (about 1.1 times the human dose, on the basis of body surface area) or higher in dogs also produced renal lesions including tubular atrophy, interstitial cell infiltration, chronic nephritis, and papillary necrosis.

Overdosage

Single oral doses of 800 mg/kg (about 2.2 times the recommended human dose, on the basis of body surface area) and 1800 mg/kg (about 9.7 times the recommended human dose, on the basis of body surface area) of mesalamine were lethal to mice and rats, respectively, and resulted in gastrointestinal and renal toxicity.

Example 2

Mesalamine Granules Maintain Remission In Ulcerative Colitis Subjects Who Switch from Another 5-ASA Treatment The following experiment demonstrates that 1.5 g of granulated mesalamine taken once-daily maintained remission versus placebo in ulcerative colitis (UC) subjects who switched from another 5-ASA product (78 percent of relapse-free subjects vs. 59 percent [P<0.001]). These subjects also had a greater probability of remaining relapse free after six months compared to placebo (77 percent vs. 50 percent [P<0.001] cumulative relapse-free probability).

Subjects (n=487) with documented UC remission (as defined by the revised Sutherland Disease Activity Index) received 1.5 g granulated mesalamine (four 375-mg capsules) or placebo once daily for six months. Subjects taking granulated mesalamine achieved the following results:

Overall, nearly 8 out of 10 subjects maintained remission of UC after six months (78 percent vs. 59 percent with placebo [P<0.001])

In a sub-set analysis, 305 subjects who switched from a prior 5-ASA had a higher probability of remaining relapse free after six months (77 percent vs. 50 percent [P<0.001])

Example 3

Granulated Mesalamine Improves Patient Adherence

Fewer subjects taking granulated mesalamine (28 percent) withdrew from the study versus subjects who received placebo (43 percent) due to disease relapse (12 percent vs. 20 percent for placebo) or adverse events (11 percent vs. 16 percent for placebo). For granulated mesalamine versus placebo, the most common adverse events were UC flare (11 percent vs. 24 percent), headache (11 percent vs. 8 percent), and diarrhea (8 percent vs. 7 percent). Incidence of renal, hepatic, and pancreatic AEs was low and comparable in both the granulated mesalamine (6%) and placebo (5%) groups. The percentage of subjects who experienced serious adverse events was small in both the granulated mesalamine (1 percent) and placebo (two percent) groups, and no event reported in the granulated mesalamine group was considered drug-related.

Example 4

Effect of Food on Absorption and Disposition of Granulated Mesalamine Formulations In another pharmacokinetics study, the effect of food intake on 5-ASA absorption was evaluated. Healthy subjects received 1.6 g of granulated mesalamine (2×0.8 g) following an overnight fast or a high-fat meal in a crossover study. $T_{max}$ for both mesalamine and N—Ac-5-ASA was prolonged following a high-fat meal. Based on an 80%:125% rule for untransformed data, the plasma $C_{max}$ for mesalamine and N—Ac-5-ASA were equivalent in fed and fasted conditions. A slight increase was seen in mesalamine $AUC_{0-inf}$ and $AUC_{0-last}$ (11% and 16%, respectively) following a high-fat meal.

The overall rate and extent of absorption of mesalamine and its N-acetyl metabolite were not affected by a high-fat meal.

Approximately 80% of an administered oral dose of mesalamine is estimated to be available in the colon, sigmoid, and rectum when dosed as mesalamine granules.

Example 5

Studies on Remission from Ulcerative Colitis

Studies were conducted in 562 adult subjects in remission from ulcerative colitis. Ulcerative colitis disease activity was assessed using a modified Sutherland Disease Activity Index1 (DAI), which is a sum of four subscores based on stool frequency, rectal bleeding, mucosal appearance on endoscopy, and physician's rating of disease activity. Each subscore can range from 0 to 3, for a total possible DAI score of 12.

At baseline, approximately 80% of subjects had a total DAI score of 0 or 1.0. Subjects were randomized 2:1 to receive either granulated mesalamine formulation 1.5 g or placebo once daily in the morning for six months. Relapse, as used herein, included, for example, a rectal bleeding subscale score of 1 or more and a mucosal appearance subscale score of 2 or more using the DAI. The analysis of the intent-to-treat population was a comparison of the proportions of subjects who remained relapse-free at the end of six months of treatment. In both studies, the proportion of subjects who remained relapse-free at six months was greater for granulated mesalamine formulation than for placebo.

TABLE 2

Percentage of Subjects Relapse-Free through 6 Months in granulated mesalamine formulation Maintenance Studies

|  | Granulated mesalamine formulation 1.5 g/day % (# no relapse/N) | Placebo % (# no relapse/N) | Difference (95% C.I.) | P-value |
|---|---|---|---|---|
| Study 1 | 68% (143/209) | 51% (49/96) | 17% (5.5, 29.2) | <0.001 |
| Study 2 | 71% (117/164) | 59% (55/93) | 12% (0, 24.5) | 0.046 |

Example 6

Measurement of Steady State Plasma Concentrations and Comparison to ASACOL® Mesalamine Formulation Steady state plasma concentrations of 5-ASA and N—Ac-5-ASA as measured by $C_{max}$ were higher following granulated mesalamine formulation administered QD compared to BID.

The time to maximum drug concentrations was shorter for granulated mesalamine formulation administered QD than BID for 5-ASA (mean of 3.96 vs. 11.00 hours, respectively) and for N—Ac-5-ASA (mean of 5.21 vs. 11.68 hours, respectively).

In a study of 3 treatments in 3 study periods, each separated by a minimum washout of 7 days, treatments were administered orally, and were as follows:

Treatment A: Asacol® 800 mg (2×400 mg tablets) BID for 4 days;

Treatment B: Granulated mesalamine formulation 800 mg BID for 4 days; or

Treatment C: Granulated mesalamine formulation 1600 mg (2×800 mg) QD for 4 days.

Subjects received treatments A, B, and C, with each administered during one of the three 4-day study treatment periods.

Plasma Concentrations

Presumably because of the number of subjects with unreleased Asacol® in their feces, there was considerable inter-subject variability in systemic exposure of 5-ASA and N—Ac-5-ASA as measured by the presumed steady state $C_{max}$ and AUC on Day 4 in the Asacol® group compared with the granulated mesalamine formulation groups. The variability in $C_{max}$ between subjects was higher with Asacol® (CV=129.7%) compared to the granulated mesalamine formulation BID and QD (CV=39.0% for the granulated mesalamine formulation BID, 55.0% for the granulated mesalamine formulation QD). The same trend in variability between subjects was observed in the AUC of 5-ASA and N—Ac-5-ASA.

Table 3 shows the pharmacokinetic data in μmol. This study showed that the steady state plasma concentrations of 5-ASA and N—Ac-5-ASA as measured by $C_{max}$ were higher following granulated mesalamine formulation administered QD compared to BID (ratios 153% and 118%, respectively; p=0.022 for 5-ASA). Plasma concentrations were assumed to be at steady state because the $T_{1/2}$ values for 5-ASA and N—Ac-5-ASA after a 1600 mg granulated mesalamine formulation dose to fasted subjects, were 5.49 hours and 10.05 hours, respectively.

The time to maximum drug concentrations was shorter for granulated mesalamine formulation administered QD than BID for 5-ASA (mean of 3.96 vs. 11.00 hours, respectively) and for N—Ac-5-ASA (mean of 5.21 vs. 11.68 hours, respectively).

TABLE 3

Plasma Pharmacokinetic Parameters for 5-ASA and N-Ac-5-ASA with Different Treatments (Day 4) (Mean ± SD, in μmol)

|  | Treatment A Asacol 800 mg BID n = 28 | Treatment B MP 800 mg BID n = 28 | Treatment C MP 1600 mg QD n = 28 | C/B Ratio (90% CI) p value[a] |
|---|---|---|---|---|
| $C_{max}$ (μmol/L) |  |  |  |  |
| 5-ASA | 6.93 ± 8.99 (129.7% CV) | 11.92 ± 4.65 (39.0% CV) | 19.87 ± 10.92 (55.0% CV) | 153 (113, 208) p = 0.022 |
| N-Ac-5-ASA | 12.01 ± 9.22 (76.8% CV) | 18.53 ± 6.31 (34.1% CV) | 23.06 ± 9.35 (40.6% CV) | 118 (98, 143) p = 0.141 |
| AUC (μmol * h/L)[b] |  |  |  |  |
| 5-ASA | 54.50 ± 49.01 (89.9% CV) | 97.00 ± 35.92 (35.9% CV) | 96.49 ± 42.40 (43.9% CV) | 96 (76, 121) p = 0.775 |
| N-Ac-5-ASA | 157.54 ± 114.12 (72.4% CV) | 237.79 ± 79.13 (33.3% CV) | 235.13 ± 101.09 (43.0% CV) | 93 (78, 112) p = 0.535 |

TABLE 3-continued

Plasma Pharmacokinetic Parameters for 5-ASA and N-Ac-5-ASA with Different Treatments (Day 4) (Mean ± SD, in μmol)

| | Treatment A<br>Asacol 800 mg BID<br>n = 28 | Treatment B<br>MP 800 mg BID<br>n = 28 | Treatment C<br>MP 1600 mg QD<br>n = 28 | C/B Ratio (90% CI)<br>p value[a] |
|---|---|---|---|---|
| $T_{max}$ (h) | | | | |
| 5-ASA | 16.0 (0, 24.0) | 16.0 (0, 24.0) | 3.0 (2.0, 16.0) | |
| N-Ac-5-ASA | 16.0 (0, 24.0) | 16.0 (0, 24.0) | 3.0 (2.0, 24.0) | |

[a]ANOVA Mixed Model Effects for log-transformed $C_{max}$ and AUC p-values for $C_{max}$ and AUC associated with Geometric Mean Ratio treatment contrast.
[b]AUCC values are listed for Treatments A and B; AUC0-24 values are listed for Treatment C.
[c]Median difference and lower and upper 90% confidence interval of the median difference for the treatments indicated.

TABLE 4

Plasma Pharmacokinetic Parameters for 5-ASA and N-Ac-5-ASA with Different Treatments (Day 4) (Mean ± SD, in μg)

| | Treatment A<br>Asacol 800 mg BID<br>n = 28 | Treatment B<br>MP 800 mg BID<br>n = 28 | Treatment C<br>MP 1600 mg QD<br>n = 28 | C/B Ratio (90% CI)<br>p value[a] |
|---|---|---|---|---|
| $C_{max}$ (μg/L)[b,c] | | | | |
| 5-ASA | 1.06 ± 1.37 | 1.82 ± 0.71 | 3.04 ± 1.67 | 153 (113, 208)<br>p = 0.022 |
| N-Ac-5-ASA | 2.34 ± 1.80 | 3.61 ± 1.23 | 4.50 ± 1.82 | 118 (98, 143)<br>p = 0.141 |
| AUC (μg * h/L)[d] | | | | |
| 5-ASA | 8.34 ± 7.50 | 14.84 ± 5.50 | 14.76 ± 6.49 | 96 (76, 121)<br>p = 0.775 |
| N-Ac-5-ASA | 30.72 ± 22.25 | 46.37 ± 15.43 | 45.85 ± 19.71 | 93 (78, 112)<br>p = 0.535 |
| $T_{max}$ (h) | | | | |
| 5-ASA | 16.0 (0, 24.0)[e] | 16.0 (0, 24.0) | 3.0 (2.0, 16.0) | |
| N-Ac-5-ASA | 16.0 (0, 24.0) | 16.0 (0, 24.0) | 3.0 (2.0, 24.0) | |

[a]ANOVA Mixed Model Effects for log-transformed $C_{max}$ and AUC p-values for $C_{max}$ and AUC associated with Geometric Mean Ratio treatment contrast.
[b]$C_{max}$ and AUC values were converted from μmol/L and μmol * h/L to μg/mL and μg * h/mL by multiplying by 0.153
[c]$C_{max}$ and AUC values were converted from μmol/L and μmol * h/L to μg/mL and μg * h/mL by multiplying by 0.195.
[d]AUC values for Treatments A and B are AUCC and for Treatment C are $AUC_{0-24}$. $AUC_C = AUC_{0-12} \times (1 + (AUC_{12-24}/AUC_{0-12}))$.
[e]Median (range).

Asacol® was administered as 800 mg BID for 4 days, the granulated mesalamine formulation was administered as 800 mg BID for 4 days. The granulated mesalamine formulation was also administered as 1600 mg QD for 4 days. Intact and partially intact Asacol® tablets were observed in fecal samples and removed from the feces of approximately 50% of subjects who were administered Treatment A (Asacol®). Because of this, and the inability of the analysis method to differentiate between released and total mesalamine in fecal samples, quantitative comparisons between Treatment A (Asacol®) and the granulated mesalamine formulation regimens were not possible.

Comparisons between the granulated mesalamine formulation QD and BID regimens showed that systemic exposure to 5-ASA and N—Ac-5-ASA were comparable. However, maximum plasma concentration of 5-ASA was greater for the QD regimen (ratio=153, p=0.022) and the time to maximum plasma concentration was shorter (3.96 versus 11.00 hours). Time to maximum concentration was considerably longer for granulated mesalamine formulation BID than for granulated mesalamine formulation QD (median 16 h vs. 3 h, respectively, for both 5-ASA and N—Ac-5-ASA). Because time was measured from when the first dose was administered, and the second BID dose was given 12 hours later, the 16 h median $T_{max}$ means that maximum plasma concentration was reached approximately 4 h after the second of the 2 BID doses. This is consistent with maximum plasma concentration being reached approximately 3 h following the single QD dose.

A study was also conducted to evaluate the effect of once and twice daily dosing of granulated mesalamine formulation 1600 mg (QD or 800 mg BID) compared to Asacol® 800 mg BID on cumulative fecal excretion, cumulative urinary excretion, and systemic exposure of 5-ASA and N—Ac-5-ASA.

Each treatment regimen lasted for 4 days and was followed by at least a 7 day washout period.

Intact and partially intact Asacol® tablets were observed in fecal samples and removed from the feces of approximately 50% of subjects who were administered Treatment A (Asacol®). Comparisons between the granulated mesalamine formulation groups showed maximum plasma concentration of 5-ASA was greater for the QD regimen (ratio=153, p=0.022) and the time to maximum plasma concentration was shorter (3.96 versus 11.00 hours).

Time to maximum concentration was considerably longer for granulated mesalamine formulation BID than for granulated mesalamine formulation QD (median 16 h vs. 3 h, respectively, for both 5-ASA and N—Ac-5-ASA).

Granulated mesalamine pellets were safe and well tolerated in healthy adult volunteers when administered orally once daily (1600 mg QD). Steady state plasma concentrations of 5-ASA and N—Ac-5-ASA as measured by $C_{max}$ were higher following granulated mesalamine formulations administered QD compared to BID. Plasma concentrations were assumed to be at steady state because the $T_{1/2}$ values for 5-ASA and N—Ac-5-ASA in study granulated mesalamine formulation PK1002, after a 1600 mg dose to fasted subjects, were 5.49 h and 10.05 h, respectively. The time to maximum drug concentrations was shorter for granulated mesalamine formulations administered QD than BID for 5-ASA (mean of 3.96 h vs. 11.00 h, respectively) and for N—Ac-5-ASA (mean of 5.21 h vs. 11.68 h, respectively).

Example 7

Comparison of Dosing Regimens and Effect on Ulcerative Colitis Remission

Treatment I: Oral administration of Salofalk® granules 1.5 g once daily in the morning on Days 1, and 4 to 10. No administration on Days 2 and 3.

Treatment II: Oral administration of Salofalk® granules 3.0 g once daily in the morning on Days 1, and 4 to 10. No administration on Days 2 and 3.

Treatment III: Oral administration of Salofalk® granules 0.5 g thrice daily on Days 1 to 6. Last dosing in the morning of Day 7.

Treatment IV: Oral administration of Salofalk® granules 1.0 g thrice daily on Days 1 to 6. Last dosing in the morning of Day 7.

Both three gram granulated mesalamine formulation once daily and 1 g granulated mesalamine formulation TID showed good efficacy in subjects with active ulcerative colitis, and 3 g granulated mesalamine formulation QD given as single morning dose proved to be non-inferior to 1 g granulated mesalamine formulation TID.

Salofalk® granules were preferred by the study subjects over the previous use of tablets. The vast majority of the subjects preferred a QD regimen compared to the TID regimen.

The three gram granulated mesalamine formulation administered once daily (QD) was safe and well tolerated. No disadvantage in safety and tolerability in comparison with 1 g granulated mesalamine formulation TID, especially with regard to potential tubulo-toxicity, could be observed.

TABLE 5

Clinical remission rates at the interim and final analysis in the PP and ITT analysis set each:

| | | Number (%) of patients with clinical remission at the final/withdrawal examination | | Shifted asymptotic $\chi^2$ test for comparing two rates* | Difference between proportions** |
|---|---|---|---|---|---|
| | | 3 g mesalazine OD | 1 g mesalazine TID | p (one-sided) | [95% CI] |
| 1st interim analysis | PP | 81/96 (84.4%) | 78/96 (81.3%) | 0.0007 (observed) | 3.1% [−11.4%, 17.6%] |
| | ITT | 84/104 (80.8%) | 82/106 (77.4%) | 0.0007 (observed) | 3.4% [−11.4%, 18.1%] |
| Final analysis | PP | 142/171 (83.0%) | 136/174 (78.2%) | <0.0001 (overall) | 4.9% [−3.5%, 13.3%] |
| | ITT | 151/191 (79.1%) | 143/189 (75.7%) | <0.0001 (overall) | 3.4% [−5.0%, 11.8%] |

*Non-inferiority margin: 15%

**3 g granulated mesalamine formulation QD - 1 g granulated mesalamine formulation TID; asymptotic confidence interval Abbreviations:

intention-to-treat (ITT)

once daily (OD or QD) versus three times daily (TID)

observed one-sided p-value (PP)

TABLE 6

Clinical remission rates at final analysis

| Remission | Number (%) of patients with clinical remission at the final/withdrawal examination | | Shifted asymptotic $\chi^2$ test for comparing two rates* | Difference between proportions** |
|---|---|---|---|---|
| | 3 g mesalazine OD (n = 171) | 1 g mesalazine TID (n = 174) | p (one-sided) | [95% CI] |
| Yes | 142 (83.0%) | 136 (78.2%) | <0.0001 (overall) | 4.9% [−3.5%, 13.3%] |
| No | 29 (17.0%) | 38 (21.8%) | | |

*Non-inferiority margin: 15%

**3 g granulated mesalamine formulation QD − 1 g granulated mesalamine formulation TID

TABLE 7

Clinical remission rates (ITT analysis set) at final analysis

| Remission | Number (%) of patients with clinical remission at the final/withdrawal examination | | Shifted asymptotic $\chi^2$ test for comparing two rates* p (one-sided) | Difference between proportions** [95% CI] |
|---|---|---|---|---|
|  | 3 g mesalazine OD (n = 191) | 1 g mesalazine TID (n = 189) |  |  |
| Yes | 151 (79.1%) | 143 (75.7%) | <0.0001 (overall) | 3.4% [−5.0%, 11.8%] |
| No | 40 (20.9%) | 46 (24.3%) |  |  |

*Non-inferiority margin: 15%
**3 g granulated mesalamine formulation QD − 1 g granulated mesalamine formulation TID The clinical remission rates at the final/withdrawal visit were higher in subjects taking 3 g granulated mesalamine formulation QD than in subjects taking 1 g granulated mesalamine formulation TID in both the PP and the ITT analysis set. At the final analysis, the shifted asymptotic $\chi^2$ test for comparing two rates yielded a one-sided overall p-value of <0.0001 for both the PP and the ITT analysis set for all evaluable subjects.

Dose and Mode of Administration:
3.0 g mesalazine (Salofalk® 1500 mg granules) once daily (QD).
Subjects were to administer orally:
  two sachets each containing 1.5 g mesalazine in the morning; and
  one sachet containing 1.0 g placebo both at noon and in the evening.

Clinical remission rates at the final/withdrawal visit were higher in subjects taking 3 g granulated mesalamine formulation QD than in subjects taking 1 g granulated mesalamine formulation TID. The comparison yielded a significant result. Both 3 g granulated mesalamine formulation QD and 1 g granulated mesalamine formulation TID showed efficacy in subjects with active ulcerative colitis, and 3 g granulated mesalamine formulation QD given as single morning dose proved to be non-inferior to 1 g granulated mesalamine formulation TID.

Clinical Remission (CAI)—Effects caused by Disease Severity (CAI) at Baseline

Clinical remission rates were higher in subjects with a CAI ≤8 at baseline than in subjects with a CAI >8 at baseline in both the PP and the ITT analysis set. Comparisons between treatment groups showed higher remission rates in subjects taking 3 g granulated mesalamine formulation QD than in subjects taking 1 g granulated mesalamine formulation TID in the subgroup of subjects with a CAI ≤8 at baseline. No such difference was observed in subjects with a CAI >8 at baseline.

Clinical remission rates were fairly independent of the disease localization. The highest remission rates were observed in subjects with a proctosigmoiditis and subjects with a subtotal-/pancolitis compared to subjects with a left-sided colitis in the PP and ITT analysis set. Comparisons between treatment groups showed higher remission rates in subjects taking 3 g granulated mesalamine formulation QD than in subjects taking 1 g granulated mesalamine formulation TID in the subgroup of subjects with a proctosigmoiditis.

Without wishing to be bound by any particular scientific theory, a QD regimen may deliver more active substance into the more distal parts of the colon. In both subjects with a left-sided colitis and subjects with a subtotal-/pancolitis, remission rates were higher in the 3 g granulated mesalamine formulation QD group than in the 1 g granulated mesalamine formulation TID group.

Time to First Resolution of Clinical Symptoms

The mean (SD) time to first resolution of clinical symptoms (acc. to Löfberg: ≤3 stools/day; all without blood) did not show any difference between treatment groups in the PP (3 g granulated mesalamine formulation QD: 14.9 (14.5) days, n=147; 1 g granulated mesalamine formulation TID: 15.0 (13.3) days, n=149) and ITT analysis set (3 g granulated mesalamine formulation QD: 14.9 (14.6) days, n=161; 1 g granulated mesalamine formulation TID: 15.0 (13.5) days, n=158).

According to the time to event analysis, the median time to first resolution of clinical symptoms appeared to be lower in subjects taking 3 g granulated mesalamine formulation QD than in subjects taking 1 g granulated mesalamine formulation TID.

TABLE 8

Clinical remission rates by localization of the disease

| | Number (%) of patients with clinical remission at the final/withdrawal examination by localisation of the disease | | | |
|---|---|---|---|---|
| | PP | | ITT | |
| | 3 g mesalazine OD | 1 g mesalazine TID | 3 g mesalazine OD | 1 g mesalazine TID |
| Proctosigmoiditis | 79/88 (89.8%) | 71/95 (74.7%) | 83/97 (85.6%) | 73/100 (73.0%) |
| Left-sided colitis | 36/50 (72.0%) | 28/36 (77.8%) | 40/55 (72.7%) | 30/40 (75.0%) |
| Subtotal-/pancolitis | 27/33 (81.8%) | 37/43 (86.0%) | 28/39 (71.8%) | 40/49 (81.6%) |

TABLE 9

Time to first resolution of clinical symptoms (time to event analysis)

|  | Median time to first resolution of clinical symptoms [days] | | Hazard ratio | 95% confidence interval |
|---|---|---|---|---|
|  | 3 g mesalazine OD | 1 g mesalazine TID | | |
| PP | 12.0 | 16.0 | 0.986 | [0.785, 1.239] |
| ITT | 12.0 | 16.0 | 0.961 | [0.771, 1.197] |

Example 8

Effect of Prognostic Factors on Maintenance of Remission from Ulcerative Colitis in Patients Treated with Once-Daily Mesalamine Granules (1.5 g)

Once daily dosing of mesalamine granules (GM) in a 1.5 g dosage was found to increase the time that subjects remained relapse free. In two double-blind, placebo-controlled, phase 3 studies (RCTs), more patients taking 1.5 g granulated mesalamine remained relapse-free for 6 months vs placebo (79.4% versus 63.0%; odds ratio, 2.261; 95% CI, 1.535-3.331; p<0.0001). Patients took the 1.5 g of GM as four capsules of 375 mg GM. This analysis investigates the potential effect of prognostic factors in contributing to UC relapse and the subsequent protective effect of GM vs placebo.

Pooled patients (N=562) from two independent RCTs, with documented UC remission (revised Sutherland Disease Activity Index [DAI] subscores: rectal bleeding 0; mucosal appearance <2) were randomized 2:1 to receive GM 1.5 g once daily (N=373) or placebo (N=189) for 6 months. The primary efficacy endpoint was the proportion of patients who remained relapse-free after 6 months of treatment (relapse defined as a rectal bleeding subscore ≥1 and a mucosal appearance subscore ≥2 per DAI; UC flare or UC symptoms leading to withdrawal; or initiated medication used to treat UC). Prognostic factors that may contribute to UC relapse include baseline demographics and disease characteristics such as age; sex; DAI total score, and subscores for stool frequency, mucosal appearance, physician's assessment; time to last flare; and disease duration. Covariate analysis was used to evaluate outcomes.

Demographics and baseline characteristics were similar between groups. Independent predictors of relapse included DAI score (p=0.0217), stool frequency subscore (p=0.0106), mucosal appearance score (p=0.0007), and physician's global UC assessment score (p=0.0136). After controlling for these prognostic factors in a multivariate analysis, the most influential prognostic factor for maintenance of remission was the DAI mucosal subscore (p=0.0032). Also, the effect of GM on maintenance of remission yielded a higher incidence of relapse-free patients versus placebo (odds ratio, 2.089; 95% CI, 1.407-3.103; p=0.0003).

GM dosed at 1.5 g once daily demonstrated a significant protective effect for long-term maintenance of remission of UC during the 6-month treatment period after controlling for prognostic factors. The most influential prognostic factor was the mucosal score at baseline. Even in the presence of significant, competing, prognostic factors, GM significantly increased the incidence of relapse-free patients versus placebo.

Example 9

Long Term Maintenance with Mesalamine Granules (1.5 g) in Patients Previously Treated with Corticosteroids is Associated with a Low Incidence of Ulcerative Colitis-Related Adverse Events It was also discovered that more patients that were previously treated with corticosteroids and then placed on a once daily dose of granulated mesalamine in comparison to placebo-treated patients remained relapse-free for 6 months (77% vs 55%; p<0.004). Patients took the 1.5 g of GM as four capsules of 375 mg GM. This is of interest because patients in remission with UC who receive corticosteroids often experience a relapse of symptoms during steroid tapering or soon after steroid discontinuation. The current analysis evaluates data from these steroid-treated subjects who continued in a 24-month, open-label extension (OLT), to explore the long term impact of GM on their UC symptoms and other safety parameters.

Pooled patients (N=562) from two independent RCTs, with documented UC remission (revised Sutherland Disease Activity Index [DAI] subscores: rectal bleeding 0; mucosal appearance <2) were randomized 2:1 to receive GM 1.5 g QD (N=373) or placebo (N=189) once daily for 6 months. In these trials, 158 (GM, n=105; placebo, n=53) patients with UC previously received corticosteroids (≥30 days before screening: 78% on oral steroids, 23% on enemas, and 4% on foam/suppositories) to treat UC flares or to maintain UC remission. 74 GM-treated subjects continued GM treatment into OLT and were followed for up to 30 months.

In the corticosteroid subpopulation, GM reduced the risk of treatment emergent adverse events (TEAE) of UC, and UC related symptoms (hematochezia and increased bowel frequency), over 6 months of double-blind treatment (hazard ratio 0.508, 95% CI 0.307, 0.842; p=0.0086). This low probability of recurrence of UC and UC symptoms was sustained during OLT. Adverse event rates were comparable between GM and placebo treatments in this subpopulation for related treatment-emergent AEs (3.0 vs 2.1), serious AEs (0.025 vs 0.06), and AEs leading to premature withdrawal (0.075 vs 0.06) during RCT, and declined for the GM treated patients during OLT. Mean compliance with the once-daily regimen was >96.7% during the 6 months of double-blind treatment and >96.3% during OLT.

Patients with UC who were previously treated with corticosteroids and then treated with GM (1.5 g QD) during RCT showed a low incidence of UC-related adverse events during RCT. This low risk was sustained over 30 months of treatment in the OLT.

Patients (n=209 GM, n=96 placebo) in remission with ulcerative colitis (revised Sutherland Disease Activity Index [SDAI] rectal bleeding=0, mucosal appearance <2) took mesalamine granules 1.5 g once daily or placebo for up to 6 months. The primary endpoint was the proportion of patients relapse free at Month 6 (end of treatment). Relapse was defined as SDAI rectal bleeding score ≥1 and a mucosal appearance score ≥2 an ulcerative colitis flare, or initiation of medication previously used to treat an ulcerative colitis flare.

The proportion of patients relapse free at Month 6 (end of treatment) was higher with GM than placebo (78.9% versus 58.3%, P<0.001) in the intent-to-treat analysis as well as in a more conservative supplemental analysis that evaluated all patients who prematurely withdrew from the study for any reason as having relapsed (68% versus 51%, P<0.001). Statistically significant differences (p≤0.008) favoring GM over placebo were also observed for nearly all secondary efficacy endpoints including the percentages of patients with each level of change from baseline in rectal bleeding score, physician's rating of disease activity, and stool frequency on the SDAI at Months 1, 3, and 6/end of treatment; mean change from baseline in the SDAI at Month 6/end of treatment; the percentage of patients classified as a treatment; and relapse-free duration. For the remaining secondary efficacy endpoint, the proportion of patients at each level of change from baseline in the SDAI score for mucosal appearance, numerical results favored GM, but were not significant at the P≤0.05 level (P=0.098). The only adverse events reported in 10% of patients in either treatment group were worsening ulcerative colitis (11% mesalamine granules, 27% placebo) and headache (11% mesalamine granules, 7% placebo).

Example 10

Once Daily Dosing of Granulated Mesalamine Capsules was Effective

Once-daily GM in a 1.5 g dose was found to be effective versus placebo with a favorable safety profile in the long-term maintenance of remission of ulcerative colitis. Patients took the 1.5 g of GM as four capsules of 375 mg GM. Treatment with GM maintained remission in approximately 80% of patients (165 of 209) for 6 months.

Ulcerative colitis is a chronically relapsing and remitting inflammatory bowel disease that impairs patients' quality of life, disrupts the ability to undertake daily activities, and is associated with heightened risk of morbidity and mortality from other digestive diseases including colon cancer. Long-term maintenance of remission of symptoms and mucosal inflammation is a main goal of therapy Effective maintenance of remission reduces the risk of complications and the need for surgery and improves patients' well-being and functional ability. The mainstay of therapy for the induction and maintenance of remission in patients with ulcerative colitis, 5-aminosalicylic acid (5-ASA; mesalamine) acts topically on the gastrointestinal mucosa to inhibit multiple inflammatory processes.[6] Several oral 5-ASA agents differentiated by their delivery systems have been developed with the aim of maximizing drug delivery to the colon and minimizing systemic absorption. Time- and pH-dependent delivery systems are available as are azo-bonded prodrugs that release 5-ASA in the colon upon exposure of the prodrug to colonic bacteria. When given for maintenance of remission of ulcerative colitis, 5-ASA agents are conventionally administered in multiple daily doses in various dosing schedules that may contribute to non-adherence to the therapeutic regimen, a major cause of ulcerative colitis relapse.

In one embodiment, the granulated mesalamine is dosed once daily as 4 extended-release capsules of 0.375 g mesalamine each. The gelatin capsules dissolve to release thousands of granules into the stomach. The delayed-release coating on each granule dissolves at a pH ≥6, a level frequently reached in the gastrointestinal tract. Once the delayed-release coating on each mesalamine granule dissolves, the extended-release polymer matrix core swells to distribute mesalamine gradually throughout the colon. A once-daily dose releases thousands of granules to provide substantial surface area for mesalamine release for 24-hour protection.

Men and non-pregnant, non-lactating women ≥18 years of age were eligible for the study if they had a confirmed diagnosis of mild-to-moderate ulcerative colitis in remission for at least 1 month but not more than 12 months, a history of at least one flare with symptoms that required intervention within 1 to 12 months before screening, and had not taken steroids or immunosuppressive agents within 30 days before screening. Remission was defined as both a screening rectal bleeding score of 0 (no bleeding) and a screening sigmoidoscopy score for mucosal appearance of 0 (intact mucosa with preserved or distorted vessels) or 1 (erythema, decreased vascular pattern, granularity, no mucosal hemorrhage) on the revised Sutherland Disease Activity Index (SDAI), described below. Exclusion criteria included evidence of impaired immune function; receipt of immunosuppressive therapy or corticosteroids within 30 days before screening; prior bowel surgery except appendectomy; positive serology results for human immunodeficiency virus or hepatitis B or C; presence of infectious, ischemic, or immunologic diseases involving the gastrointestinal tract; renal disease manifested by serum creatinine or blood urea nitrogen 1.5 times the upper limit of normal; liver disease manifested by values twice the upper limit of normal for alanine aminotransferase (ALT), aspartate aminotransferase (AST), alkaline phosphatase (ALP), or total bilirubin. All patients provided written informed consent.

The protocol for this randomized, double-blind, placebo-controlled, Phase III study was approved by institutional review boards for the study sites. The study included a screening phase completed within a week before randomization and a treatment phase that lasted up to 6 months. Patients who met eligibility criteria during the screening phase were randomized 2:1 to receive GM 1.5 g once daily (dosed as 4 capsules, 0.375 g mesalamine each) or matching placebo in a double-blinded fashion for up to 6 months during the treatment phase.

The treatment phase included 4 clinic visits at randomization (baseline) on Day 1 and at the end of Months 1, 3, and 6 to assess disease activity and monitor patients for adverse events. In addition, a sigmoidoscopy was performed at screening and at the end of Month 6 (or upon premature withdrawal from the study). Disease activity was assessed with the SDAI, which evaluates stool frequency, rectal bleeding, mucosal appearance, and physician's rating of disease severity on scales of 0 to 3 with a maximum total score of 12. All 4 components of SDAI were evaluated at screening and Month 6 (or upon premature withdrawal from the study); an abbreviated SDAI including all indices except mucosal appearance were evaluated on Day 1 (baseline) and at the end of Months 1 and 3. Medications prohibited during the treatment phase included, but were not limited to, immunosuppressants, chronic nonsteroidal anti-inflammatory drugs, corticosteroids, oral antibiotics except as 7- to 10-day courses for conditions unrelated to ulcerative colitis, psyllium-containing intestinal regulators, and 5-ASAs other than study medication.

If at any time during the study a patient experienced a disease flare, including rectal bleeding, an unscheduled visit was to occur. The patient was considered to have experienced a relapse and was discontinued from the study in the event of a sigmoidoscopy score for mucosal appearance and a rectal bleeding score ≥1 on the SDAI.

Efficacy data were analyzed for the Intent-to-Treat (ITT) population, defined as randomized patients who received at least 1 dose of study medication. The primary efficacy endpoint was the percentage of patients who remained relapse free after 6 months of treatment. Relapse or treatment failure was defined as a rectal bleeding score ≥1 and a mucosal appearance score ≥2 on the SDAI, an ulcerative colitis flare, or initiation of medication previously used to treat an ulcerative colitis flare. Other research in ulcerative colitis has employed similar, but less inclusive, definitions of relapse.[20] In the primary efficacy analysis, premature withdrawal from the study was not considered to be a relapse unless the reason for early termination was lack of efficacy or an ulcerative colitis-related adverse event. For patients prematurely withdrawing from the study for other reasons, the last SDAI assessment was used to determine relapse status.

The treatment groups were compared on the primary endpoint with a Cochran-Mantel-Haenszel test controlled for country. In sample-size calculations, it was estimated that 200 patients in the group receiving GM and 100 patients in the placebo group would provide ≥90% power (beta=0.10) to reject the null hypothesis of no difference between treatment groups with a 2-sided significance level of 5% (α=0.05), a 2:1 allocation ratio, and the assumption of a relapse-free rate of 70% with GM and 50% with placebo.

Secondary efficacy endpoints were the percentages of patients with each level of change from baseline in rectal bleeding score, mucosal appearance score, physician's rating of disease activity, and stool frequency on the SDAI at Months 1, 3, and 6/end of treatment; mean change from baseline in the SDAI at Month 6/end of treatment; the percentage of patients classified as treatment successes, defined as maintaining the SDAI total score ≤2 with no individual component >1 and rectal bleeding score of 0 at Month 6/end of treatment; and relapse-free duration, defined as the number of days between the start of study medication and the date of first relapse or premature withdrawal from the study plus 1 day. The last-observation-carried-forward (LOCF) methodology was used for imputing missing values for secondary efficacy endpoints for patients who prematurely withdrew from the study.

Statistical testing of the secondary endpoints was performed in a predefined hierarchical fashion until a nonsignificant P-value was identified (P>0.05), after which point significance tests were considered exploratory. Differences between treatment groups were tested with a Cochran-Mantel-Haenszel test controlled for country for the categorical variables and with analysis of covariance (ANCOVA) adjusted for baseline value and country for mean change from baseline in the SDAI at Month 6/end of treatment. For relapse-free duration, a Cox proportional hazards regression model adjusted for country was used to assess differences between treatment groups, and Kaplan-Meier methods were used to calculate cumulative relapse-free probability estimates for each treatment group at Months 1, 3, and 6. Chi-square tests were used to identify the week at which GM separated from placebo with respect to relapse-free probability.

Safety data were summarized with descriptive statistics for the Safety population, defined as randomized patients who received at least 1 dose of study medication and provided at least 1 post-baseline safety assessment. The main safety measures were the percentages of patients with treatment-emergent adverse events (defined as any untoward medical occurrences with a start date on or after treatment Day 1 or, if pre-existing, worsening after treatment Day 1), serious adverse events (defined as adverse events that resulted in death, disability, or incapacity; were life threatening; required or prolonged hospitalization; or were a congenital anomaly or birth defect), adverse events leading to premature withdrawal from the study, and the results of clinical laboratory tests.

Demographics, baseline clinical characteristics, and compliance were summarized with descriptive statistics. Compliance was calculated as 100*(number of capsules dispensed−number of capsules returned)/(4*number of days of exposure).

Of 356 individuals screened for the study, 305 were randomized to treatment (n=209 GM, n=96 placebo). All 305 randomized patients received at least one dose of study medication and were therefore included in the ITT population. Five (5) of these 305 patients did not return a post-baseline safety assessment; therefore, 300 patients were included in the Safety population. FIG. 1 shows patient disposition. The frequency of premature withdrawal from the study was lower in the group receiving GM (31.1%) than the placebo group (49.0%). The most common reasons for premature withdrawal were adverse events and lack of efficacy.

Demographics and baseline disease characteristics were similar between the group receiving GM and the placebo group (Table 10). The majority of patients were white, and 44.0% (GM) to 55.2% (placebo) were male. The mean time since the most recent ulcerative colitis flare was 25.6 weeks in both groups, and the mean duration of remission was approximately 16 weeks. The mean baseline SDAI score was 0.8 (SD 0.8) in the group receiving GM and 1.0 (SD 1.3) in the placebo group.

TABLE 10

Demographics and Baseline Disease Characteristics

| | Mesalamine Granules (n = 209) | Placebo (n = 96) |
| --- | --- | --- |
| Demographics | | |
| Age, years: mean (SD) | 46.9 (13.6) | 45.5 (14.4) |
| Male: n (%) | 92 (44.0) | 53 (55.2) |
| Race: *n (%) | | |
| American Indian/Alaskan Native | 4 (1.9) | 0 (0.0) |
| Asian | 1 (0.5) | 0 (0.0) |
| Black/African American | 19 (9.1) | 11 (11.5) |
| White | 188 (90.0) | 85 (88.5) |
| Body mass index, kg/m$^2$: mean (SD) | 26.79 (5.53) | 26.43 (5.31) |
| Disease Characteristics | | |
| Duration of disease, weeks: mean (SD) | 310.0 (321.9) | 312.5 (310.7) |
| Time since last flare, weeks: mean (SD) | 25.6 (13.0) | 25.6 (13.0) |
| Duration of current remission, weeks: mean (SD) | 16.8 (11.1) | 16.2 (11.0) |
| Baseline SDAI scores: mean (SD) | | |
| Total | 0.8 (0.8) | 1.0 (1.3) |
| Stool frequency | 0.1 (0.2) | 0.1 (0.4) |
| Rectal bleeding | 0.0 (0.0) | 0.0 (0.2) |
| Mucosal appearance | 0.5 (0.5) | 0.7 (0.5) |
| Physician's rating of severity | 0.2 (0.4) | 0.2 (0.5) |

*Patients could indicate more than 1 racial category and therefore could be represented in more than 1 category.

The mean compliance for the duration of the treatment period was 96.2% (SD 11.6) for the group receiving GM and 96.7% (SD 6.4) for the placebo group.

Figure 2:
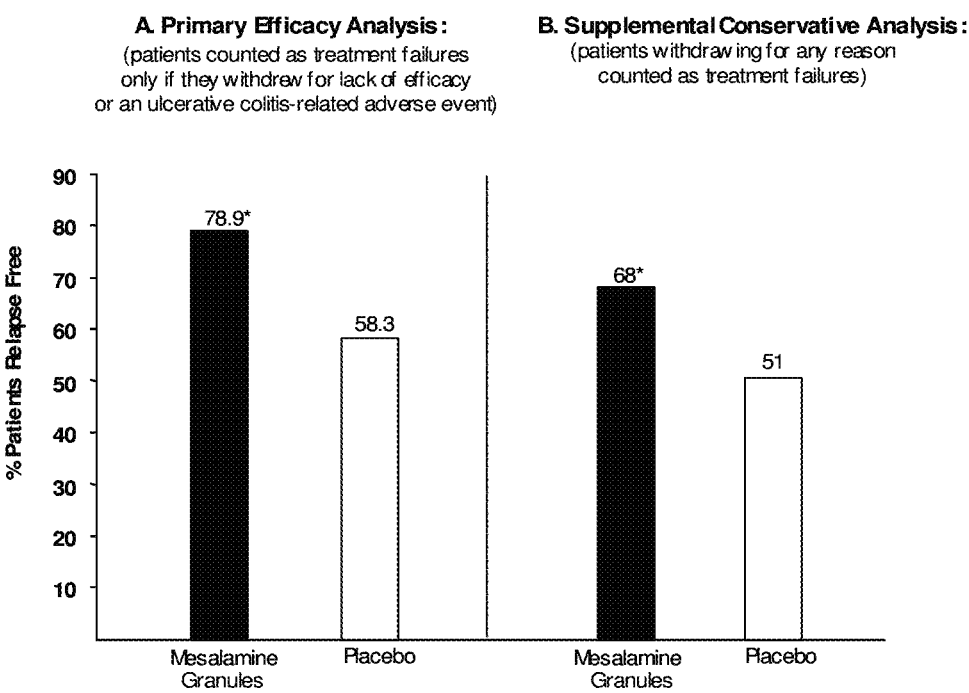
FIG. 2 shows percentage of patients relapse free at Month 6/end of treatment.

In the efficacy analysis, the proportion of patients who were relapse free at Month 6/end of treatment was significantly higher in the group receiving GM compared with the placebo group (78.9% versus 58.3%, P<0.001) (FIG. 2A). In this analysis, patients who prematurely withdrew from the study were not counted as having relapsed unless they withdrew for lack of efficacy or an ulcerative colitis-related adverse event. Likewise, in a more conservative supplemental analysis, which evaluated all patients who prematurely withdrew from the study for any reason as having relapsed, the proportion of patients who were relapse free at Month 6/end of treatment was significantly higher in the group receiving GM compared with the placebo group (68% versus 51%, P<0.001) (FIG. 2B).

Figure 3:
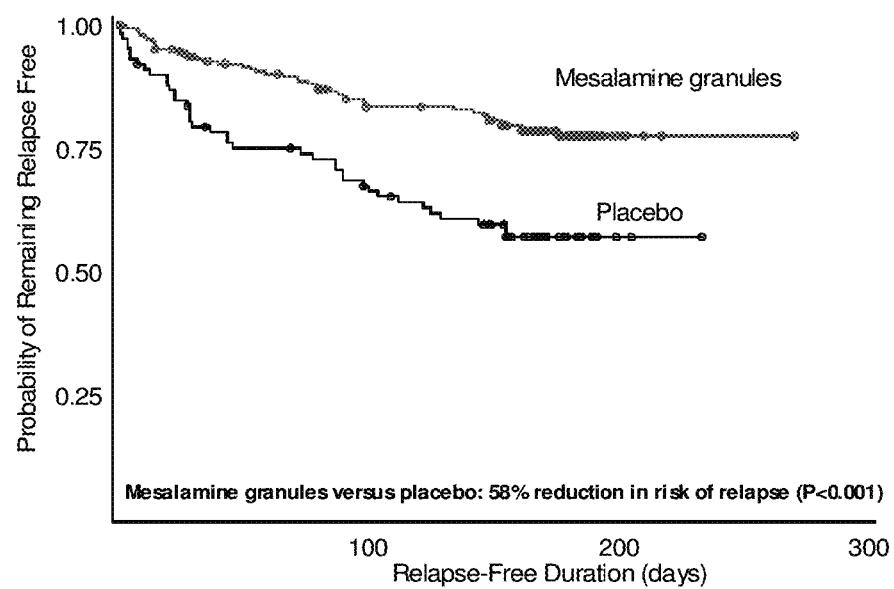
FIG. 3 shows Kaplan-Meier estimates of time to relapse during the treatment period in the ITT population.

The hazard ratio for the risk of relapse in the group receiving GM relative to that in the placebo group reflected a 58% reduction in the risk of relapse with GM compared with placebo over the 6-month treatment period (FIG. 3). For the probability of remaining relapse free, GM first statistically significantly separated from placebo during the first week of treatment. A number-needed-to-treat analysis revealed that 1 ulcerative colitis relapse was prevented for every 5 patients treated with GM.

Statistically significant differences favoring GM capsules over placebo were observed for other efficacy endpoints including the proportions of patients at each level of change from baseline in the SDAI scores for rectal bleeding (P=0.008), physician's rating of disease activity (P=0.005), and stool frequency (P=0.005); the proportion of patients classified as treatment successes (P=0.003); mean change from baseline in the SDAI total score (P=0.001); and probability of remaining relapse free over 6 months (P<0.001) (Table 11). For the remaining secondary efficacy endpoint, which was the proportion of patients at each level of change from baseline in the SDAI score for mucosal appearance, numerical results favored GM, but were not significant at the P≤0.05 level (P=0.098) (Table 11).

TABLE 11

Summary of Results for Other Efficacy Endpoints*

|  | Mesalamine Granules (n = 209) | Placebo (n = 96) | P-value |
|---|---|---|---|
| Change from baseline in rectal bleeding score at Month 6/end of treatment, n (%) |  |  | 0.008 |
| −1 | 0 (0.0) | 1 (1.0) |  |
| 0 | 170 (81.3) | 64 (66.7) |  |
| 1 | 22 (10.5) | 11 (11.5) |  |
| 2 | 16 (7.7) | 19 (19.8) |  |
| 3 | 1 (0.5) | 1 (1.0) |  |
| Change from baseline in mucosal appearance at Month 6/end of treatment, n (%) |  |  | 0.098 |
| −1 | 32 (15.3) | 13 (13.5) |  |
| 0 | 129 (61.7) | 51 (53.1) |  |
| 1 | 32 (15.3) | 20 (20.8) |  |
| 2 | 14 (6.7) | 11 (11.5) |  |
| 3 | 2 (1.0) | 1 (1.0) |  |
| Change from baseline in physician's rating of disease at Month 6/end of treatment | 1 (0.5) | 0 (0.0) | 0.005 |
| −1 | 16 (7.7) | 6 (6.3) |  |
| 0 | 146 (69.9) | 55 (57.3) |  |
| 1 | 35 (16.7) | 17 (17.7) |  |
| 2 | 10 (4.8) | 18 (18.8) |  |
| 3 | 1 (0.5) | 0 (0.0) |  |
| Maintenance of SDAI ≤2 with no individual component >1 and rectal bleeding = 0 at Month 6, n (%) | 147 (70.3) | 51 (53.1) | 0.003 |
| Mean (SD) change from baseline in the SDAI at Month 6/end of treatment | 0.9 (2.4) | 2.0 (3.3) | 0.001 |
| Month 6 cumulative relapse-free probability (SE) | 0.77 (0.03) | 0.56 (0.05) | <0.001 |
| Change from baseline in stool frequency at Month 6/end of treatment |  |  | 0.005 |
| −1 | 4 (1.9) | 1 (1.0) |  |
| 0 | 167 (79.9) | 64 (66.7) |  |
| 1 | 20 (9.6) | 11 (11.5) |  |
| 2 | 8 (3.8) | 11 (11.5) |  |
| 3 | 10 (4.8) | 9 (9.4) |  |

The percentage of patients with ≥1 treatment-emergent adverse event was 64% in each treatment group. The only treatment-emergent adverse events reported in ≥10% of patients in either treatment group were worsening ulcerative colitis (11% GM, 27% placebo) and headache (11% GM, 7% placebo). Table 12 lists treatment-emergent adverse events reported in ≥3% of patients in a treatment group and reported more frequently with GM than placebo.

TABLE 12

Treatment-Emergent Adverse Events Reported in ≥3% of Patients in a Treatment Group and Reported More Frequently with Mesalamine Granules than Placebo

|  | Mesalamine Granules n = 206 n (%) | Placebo n = 94 n (%) |
|---|---|---|
| Headache | 23 (11) | 7 (7) |
| Diarrhea | 18 (9) | 7 (7) |
| Abdominal pain | 15 (7) | 6 (6) |
| Nasopharyngitis | 10 (5) | 3 (3) |
| Upper abdominal pain | 8 (4) | 3 (3) |
| Abnormal feces | 7 (3) | 2 (2) |
| Back pain | 6 (3) | 2 (2) |
| Nausea | 7 (3) | 1 (1) |

Treatment-emergent adverse events affecting the pancreatic, renal, or hepatic systems were rare in both treatment groups. Only 1 adverse event involving the pancreas was reported: a mild exacerbation of acute pancreatitis not considered to be caused by study medication in a patient receiving GM. Adverse events affecting the renal and hepatic systems were similarly infrequent. Elevations in liver associated laboratory chemistries reported as treatment-emergent adverse events were less frequent in patients receiving GM than in patients receiving placebo: <1% of patients versus 4% of patients for elevated AST; 0% versus 4% for elevated ALT; and <1% versus 2% for elevated alkaline phosphatase.

In the randomized, double-blind study reported herein, 1.5 g of mesalamine granules administered in 375 mg capsules, taken once daily for up to 6 months, significantly protected against ulcerative colitis relapse versus placebo. Approximately 8 of 10 patients (78.9%) treated with the capsules of GM were relapse free for the duration of the 6-month treatment period compared with 58.3% of placebo-treated patients. Over the 6-month treatment period, GM reduced the risk of relapse by 58% compared with placebo.

A substantial protective effect of GM was observed both in the primary efficacy analysis, in which patients who prematurely withdrew from the study were not counted as having relapsed unless they withdrew for lack of efficacy or an ulcerative colitis-related adverse event, and in a more conservative supplemental analysis that evaluated all patients who prematurely withdrew from the study for any reason as having relapsed. Secondary efficacy measures support the primary efficacy analysis in demonstrating significantly greater probability of remaining relapse free over 6 months as well as significantly better scores for rectal bleeding, physician's rating of disease activity, and stool frequency with GM than placebo. Adherence to the once-daily dosing regimen was high in this study. The compliance rate with the once-daily dosing regimen exceeded 95% over the 6-month treatment period.

Besides being effective versus placebo, GM had a favourable safety profile in this study. Among adverse events reported in ≥5% of patients in either treatment group, the only adverse event occurring >2% more frequently with GM than placebo was headache (11% GM, 7% placebo). The incidence of adverse events leading to premature withdrawal from the study was nearly 2-fold lower in the group receiving GM (15%) than the placebo group (28%). The incidences of adverse events affecting the pancreatic, hepatic, and renal systems—which have been reported, albeit rarely, with other mesalamine formulations—were low in both groups and did not differ between GM and placebo. While antacids were permitted during the treatment period, only 5 patients reported concomitant antacid use in the GM group.

GM capsules administered once daily had a favorable safety profile and was effective compared with placebo in the long-term maintenance of remission of ulcerative colitis; 8 of 10 patients maintained remission for the 6-month duration of the treatment period and GM treatment resulted in significantly better scores for rectal bleeding, physician's rating of disease activity, and stool frequency than placebo. The delayed-release coating dissolves at a pH and exposes the extended-release core. The extended release core of each granule then slowly releases 5-ASA throughout the colon.

Example 11

Effect of Prognostic Factors on Maintenance of Remission from Ulcerative Colitis in Patients Treated with Once-Daily Mesalamine Granules (1.5 G)

In this example, the potential effect of prognostic factors contributing to UC relapse and the protective effect of granulated mesalamine versus placebo were investigated using pooled data from the clinical studies described above.

For the purposes of this example, remission was defined as both of the following, according to revised Sutherland Disease Activity Index (DAI): a sigmoidoscopy score (mucosal appearance index score) of 0 to 1 and a rectal bleeding score of 0.

The results are shown in Table 13 and 14.

TABLE 13

Analysis of Prognostic Factors on Maintenance of Remission of UC

| Individual prognostic factors on Maintenance of Remission of UC | p-value from Chi-square |
| --- | --- |
| Time to last flare (<24 weeks, >=24 weeks) | 0.9117 |
| Disease duration (<180 weeks, >=180 weeks) | 0.2121 |
| Dai score (0, 1) | 0.0217 |
| Stool frequency (0 vs. 1, 2, 3) | 0.0106 |
| Physicians' assessment (0 vs. 1, 2, 3) | 0.0136 |
| Mucosal score (0 vs. 1, 2, 3) | 0.0007 |
| Age (<50 years, >=50 years) | 0.0667 |
| Sex (female, male) | 0.4607 |

TABLE 14

Analysis of prognostic factors on Maintenance of Remission of UC

| Prognostic factors in the Logistic Regression Model | Odds Ratio | 95% Confidence Limit for Odds Ratio | p-value from Wald test |
| --- | --- | --- | --- |
| Treatment (Mesalamine vs. Placebo) | 2.089 | (1.407, 3.103) | 0.0003 |
| Mucosal score (0 vs. 1, 2, 3) | 1.805 | (1.219, 2.673) | 0.0032 |

As shown in Table 13 and 14, administration of 1.5 g of granulated mesalamine once daily had a significant protective effect in the long-term maintenance of remission of UC during the 6-month treatment period after controlling for prognostic factors. The data demonstrate that the most influential prognostic factor was the mucosal score at baseline.

Equivalents

Those skilled in the art will recognize, or be able to ascertain using no more than routine experimentation, many equivalents to the specific embodiments of the invention described herein. Such equivalents are intended to be encompassed by the following claims.

Incorporation By Reference

The contents of all references, patents, pending patent applications and published patents, cited throughout this application are hereby expressly incorporated by reference.

What is claimed is:

1. A method of maintaining the remission of ulcerative colitis in a subject comprising administering to the subject a granulated mesalamine formulation comprising four capsules each comprising 0.375 g of granulated mesalamine once per day in the morning, without food, wherein:
    said method maintains remission of ulcerative colitis in a subject for a period of at least 6 months of treatment;
    remission is defined as a DAI score of 0 or 1;
    the granulated mesalamine formulation is not administered with antacids; and
    wherein 85% to 90% of the mesalamine reaches the terminal ileum and colon.

2. The method of claim 1, wherein the granulated mesalamine formulation is a delayed and extended release formulation.

3. The method of claim 2, wherein delayed and extended release comprises first releasing mesalamine in the ileum and continuing to release mesalamine throughout the terminal ileum and colon.

4. The method of claim 1, wherein the granulated mesalamine formulation is administered for the maintenance of remission of ulcerative colitis in subjects 18 years of age and older.

5. The method of claim 1, further comprising advising the subject that subjects having hypersensitivity to salicylates, aminosalicylates, or any component of the granulated mesalamine formulation should not be administered the granulated mesalamine formulation.

6. The method of claim 1, further comprising advising the subject that when being administered granulated mesalamine formulation renal impairment may occur.

7. The method of claim 6, further comprising assessing the subject's renal function at one or more of the following: at the beginning of treatment, before initiating therapy, or periodically during therapy.

8. The method of claim 1, further comprising advising the subject that acute exacerbation of colitis symptoms can occur.

9. The method of claim 1, further comprising advising the subject that the granulated mesalamine formulation should be used with caution in subjects with renal disease.

10. The method of claim 1, further comprising monitoring the blood cell counts in geriatric subjects being administered the granulated mesalamine formulation.

11. The method of claim 1, further comprising advising the subject that there are adverse reactions associated with administration of the granulated mesalamine formulation.

12. The method of claim 11, wherein the adverse reactions comprise one or more of headache, diarrhea, upper abdominal pain, nausea, nasopharyngitis, flu or flu-like illness, and sinusitis.

13. The method of claim 1, further comprising advising the subject that the granulated mesalamine formulation is not expected to inhibit the metabolism of drugs that are substrates of CYP1A2, CYP2C9, CYP2C19, CYP2D6, or CYP3A4.

14. The method of claim 1, further comprising selecting a subject with a DAI score of 0 or 1 for maintaining remission of ulcerative colitis with granulated mesalamine.

15. The method of claim 1, wherein the mesalamine comprised in the formulation is released over approximately 7 hours.

16. A method of maintaining the remission of ulcerative colitis in a subject comprising advising the subject that granulated mesalamine should not be taken with antacids and administering to the subject granulated mesalamine formulation comprising four capsules each comprising 0.375 g of granulated mesalamine once per day in the morning, without food, wherein:
- said method maintains remission of ulcerative colitis in a subject for a period of at least 6 months of treatment;
- remission is defined as a DAI score of 0 or 1;
- the granulated mesalamine formulation is not administered with antacids; and
- wherein 85% to 90% of the mesalamine reaches the terminal ileum and colon.

* * * * *